(12) United States Patent
Accurso

(10) Patent No.: US 10,416,181 B2
(45) Date of Patent: *Sep. 17, 2019

(54) APPARATUS FOR REMOVING LIQUID CONTENTS OF A CONTAINER HAVING A KEY ACTIVATED SLIDING LOCK AND METHOD THEREFORE

(71) Applicant: Abbott Laboratories, Abbott Park, IL (US)

(72) Inventor: Roger W. Accurso, Fremont, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,763

(22) Filed: Nov. 17, 2017

(65) Prior Publication Data

US 2018/0156834 A1    Jun. 7, 2018

Related U.S. Application Data

(63) Continuation of application No. 15/141,187, filed on Apr. 28, 2016, now Pat. No. 9,823,263.

(Continued)

(51) Int. Cl.
   *G01N 1/28*       (2006.01)
   *G01N 35/10*      (2006.01)
   (Continued)

(52) U.S. Cl.
   CPC .......... *G01N 35/1002* (2013.01); *B01L 99/00* (2013.01); *G01N 1/28* (2013.01);
   (Continued)

(58) Field of Classification Search
   CPC .......... G01N 1/28; G01N 35/10; B01L 99/00
   (Continued)

(56) References Cited

U.S. PATENT DOCUMENTS

| 3,650,306 A | 3/1972 | Lancaster |
| 4,282,182 A | 8/1981 | Webster |

(Continued)

FOREIGN PATENT DOCUMENTS

| JP | S58501367 A | 8/1983 |
| JP | 2009517663  | 4/2009 |

(Continued)

OTHER PUBLICATIONS

International Searching Authority, "Search Report and Written Opinion," issued in connection with International Patent Application No. PCT/US2016/029743, dated Jul. 28, 2016, 13 pages.

(Continued)

*Primary Examiner* — Arlen Soderquist
(74) *Attorney, Agent, or Firm* — Hanley, Flight & Zimmerman, LLC

(57) ABSTRACT

Cradles for draining liquid from containers are described herein. An example apparatus includes a housing having a bottom wall, a side wall and an open top. The housing is to receive a container having liquid. The example apparatus includes a probe extending upward from the bottom wall toward the open top and is to drain the liquid from the container when the probe is inserted into the container. The example apparatus also includes a sliding lock slidably disposed within the housing that receives a cap or top of the container when the container is inserted into the housing. The sliding lock includes a key slot. The sliding lock is movable when a cap or top of the container has a matching key that engages the key slot, which enables the sliding lock to move downward to expose the probe and drain the liquid from the container.

20 Claims, 17 Drawing Sheets

Related U.S. Application Data

(60) Provisional application No. 62/155,768, filed on May 1, 2015.

(51) Int. Cl.
*B01L 99/00* (2010.01)
*B01L 3/00* (2006.01)

(52) U.S. Cl.
CPC .......... *G01N 35/1079* (2013.01); *B01L 3/523* (2013.01); *B01L 2200/025* (2013.01); *G01N 2035/1025* (2013.01)

(58) Field of Classification Search
USPC .................... 422/62–67; 436/43–54, 180
See application file for complete search history.

(56) References Cited

U.S. PATENT DOCUMENTS

| | | | |
|---|---|---|---|
| 4,806,316 A * | 2/1989 | Johnson | B01L 3/502 |
| | | | 422/523 |
| 4,844,870 A | 7/1989 | Rasmussen et al. | |
| 5,031,797 A | 7/1991 | Boris et al. | |
| 5,171,538 A | 12/1992 | Tremmel et al. | |
| 5,665,315 A | 9/1997 | Robert et al. | |
| 5,683,658 A | 11/1997 | Reischl et al. | |
| 5,836,482 A | 11/1998 | Ophardt et al. | |
| 5,837,203 A | 11/1998 | Godec et al. | |
| 5,885,533 A | 3/1999 | Savage et al. | |
| 5,915,427 A | 6/1999 | Grabenkort | |
| 5,947,171 A | 9/1999 | Woodruff | |
| 6,016,712 A | 1/2000 | Warden et al. | |
| 6,043,097 A | 3/2000 | Dumitrescu et al. | |
| 6,074,615 A | 6/2000 | Lewis et al. | |
| 6,085,809 A | 7/2000 | Woodruff | |
| 6,109,480 A | 8/2000 | Monsrud et al. | |
| 6,197,260 B1 | 3/2001 | Bradshaw et al. | |
| 6,305,444 B1 | 10/2001 | Woodruff | |
| 6,321,941 B1 | 11/2001 | Argentieri et al. | |
| 6,386,392 B1 | 5/2002 | Argentieri et al. | |
| 6,390,335 B1 | 5/2002 | Lawson et al. | |
| 6,440,371 B1 | 8/2002 | Dumitrescu et al. | |
| 6,475,436 B1 | 11/2002 | Schabbach et al. | |
| 6,511,634 B1 | 1/2003 | Bradshaw et al. | |
| 6,543,496 B2 | 4/2003 | Woodruff | |
| 6,607,102 B1 | 8/2003 | Griese et al. | |
| 6,685,056 B1 | 2/2004 | Argentieri et al. | |
| 6,732,772 B2 | 5/2004 | Woodruff | |
| 6,866,820 B1 | 3/2005 | Otto et al. | |
| 7,073,546 B2 | 7/2006 | Woodruff | |
| 7,182,098 B2 | 2/2007 | Tilling et al. | |
| 7,186,384 B2 | 3/2007 | Ruther et al. | |
| 7,211,437 B2 | 5/2007 | Schabbach et al. | |
| 7,402,291 B2 | 7/2008 | Fine et al. | |
| 7,458,665 B2 * | 12/2008 | Batista | B41J 2/17509 |
| | | | 222/83 |
| 7,546,857 B2 | 6/2009 | Chadbourne et al. | |
| 7,569,187 B2 | 8/2009 | Schabbach et al. | |
| 7,621,426 B2 | 11/2009 | Reynolds et al. | |
| 7,690,392 B1 | 4/2010 | Sarkiss | |
| 7,727,474 B2 | 6/2010 | Krause | |
| 7,744,817 B2 | 6/2010 | Bui | |
| 7,798,184 B2 | 9/2010 | Schultz, Jr. et al. | |
| 8,153,061 B2 | 4/2012 | Walters et al. | |
| 8,235,079 B2 | 8/2012 | Schultz, Jr. | |
| 8,268,171 B2 | 9/2012 | Liao | |
| 8,387,830 B2 | 3/2013 | Proper et al. | |
| RE44,310 E | 6/2013 | Chadbourne et al. | |
| 8,453,685 B2 | 6/2013 | Schultz, Jr. et al. | |
| 8,485,395 B2 | 7/2013 | Ciavarella et al. | |
| 8,652,407 B1 | 2/2014 | Wilson et al. | |
| 8,701,696 B2 | 4/2014 | Guala | |
| 8,708,198 B2 | 4/2014 | Proper et al. | |
| 8,999,268 B2 | 4/2015 | Egger-Cimenti et al. | |
| 9,016,145 B2 | 4/2015 | Lopez-Alvarez et al. | |
| 9,108,832 B2 | 8/2015 | Akutsu et al. | |
| 9,173,816 B2 | 11/2015 | Reinhardt et al. | |
| 9,327,955 B2 | 5/2016 | Simpson | |
| 9,403,629 B2 | 8/2016 | Accurso | |
| 9,823,263 B2 | 11/2017 | Accurso | |
| 2003/0231988 A1 | 12/2003 | Chiarin | |
| 2005/0011916 A1 * | 1/2005 | Battista | B41J 2/17509 |
| | | | 222/576 |
| 2006/0124662 A1 | 6/2006 | Reynolds et al. | |
| 2007/0116599 A1 | 5/2007 | Walters et al. | |
| 2007/0199598 A1 | 8/2007 | Schultz, Jr. et al. | |
| 2008/0142113 A1 | 6/2008 | Kiani et al. | |
| 2009/0246085 A1 | 10/2009 | Watson et al. | |
| 2012/0152392 A1 | 6/2012 | Guala | |
| 2013/0195734 A1 | 8/2013 | Yeaton et al. | |
| 2013/0263970 A1 | 10/2013 | Schultz, Jr. et al. | |
| 2014/0263316 A1 | 9/2014 | Accurso | |
| 2015/0105691 A1 * | 4/2015 | Hadvary | A61M 5/158 |
| | | | 600/567 |
| 2015/0190805 A1 | 7/2015 | Etheredge et al. | |
| 2016/0003718 A1 | 1/2016 | Ikushima et al. | |
| 2016/0318022 A1 | 11/2016 | Accurso | |

FOREIGN PATENT DOCUMENTS

| | | |
|---|---|---|
| WO | 8300932 | 3/1983 |
| WO | 2014143331 | 9/2014 |
| WO | 2015012391 | 1/2015 |
| WO | 2015109763 | 7/2015 |

OTHER PUBLICATIONS

International Bureau, "International Preliminary Report on Patentability and Written Opinion," issued in connection with International Patent Application No. PCT/US2016/029743, dated Nov. 7, 2017, 9 pages.

United States Patent and Trademark Office, "Notice of Allowance," issued in connection with U.S. Appl. No. 15/141,187, dated Jul. 5, 2017, 18 pages.

Japanese Patent Office, "Notice of Rejection", issued in connection with Japanese Application No. 2017-557051, dated Dec. 4, 2018, 6 pages.

National Intellectual Property Administration, P.R. China, "First Office Action", issued in connection with Chinese Application No. 201680038943.0 dated Jun. 25, 2019, 23 pages.

* cited by examiner

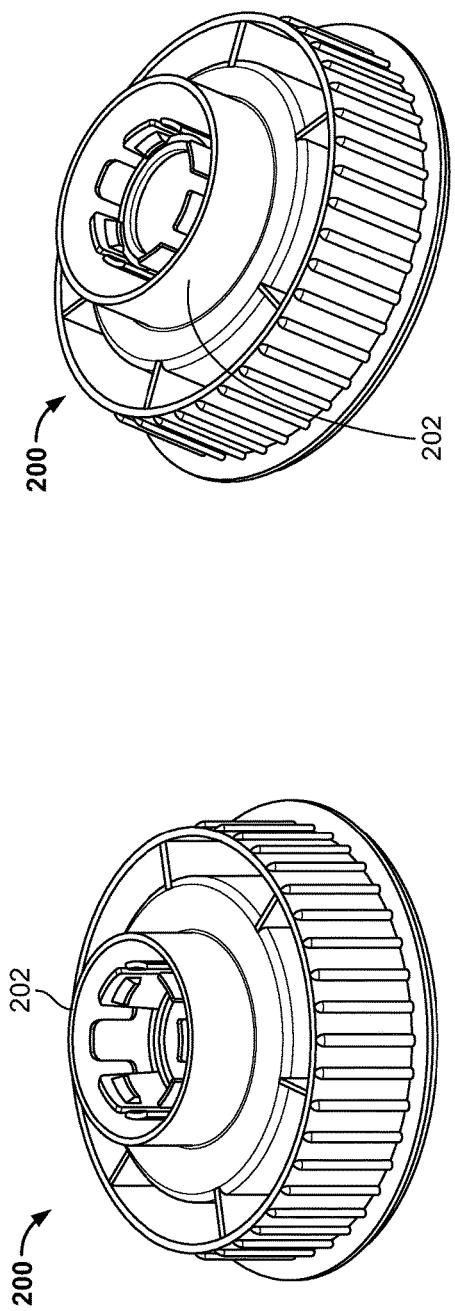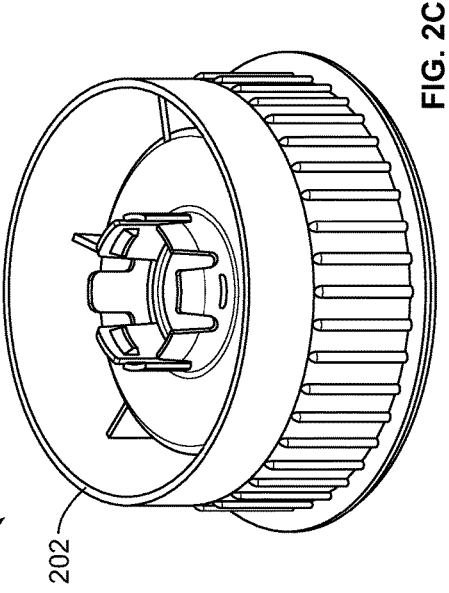

APPARATUS FOR REMOVING LIQUID CONTENTS OF A CONTAINER HAVING A KEY ACTIVATED SLIDING LOCK AND METHOD THEREFORE

RELATED APPLICATIONS

This patent arises from a continuation of U.S. application Ser. No. 15/141,187 (now U.S. Pat. No. 9,823,263), titled "Apparatus for Removing Liquid Contents of a Container Having a Key Activated Sliding Lock and Method Therefore," and filed Apr. 28, 2016, which claims the benefit under 35 U.S.C. § 119(e) to U.S. Provisional Application No. 62/155,768, titled "Apparatus for Removing Liquid Contents of a Container," and filed May 1, 2015. U.S. application Ser. No. 15/141,187 know U.S. Pat. No. 9,823,263) and U.S. Provisional Application No. 62/155,768 are incorporated herein by this reference in their entireties.

FIELD OF THE DISCLOSURE

This disclosure relates generally to containers of liquid and, more particularly, to apparatus for removing liquid contents of a container.

BACKGROUND

Healthcare diagnostics laboratories use diagnostic instruments, such as automated diagnostic analyzers, for testing and analyzing samples. Known automated diagnostic analyzers use various solutions or liquids such as reagents, wash solutions, triggers, diluents, etc. to perform the diagnostic analysis procedures. These liquids are commonly used throughout the analysis procedures and, therefore, the analyzers typically have one or more onboard containers or tanks that hold the liquids. To refill the onboard tanks, smaller bottles or containers of the solution or liquid are fluidly coupled to the tanks via screw caps with dip tube assemblies. The liquid contents are then pumped from the containers, via the dip tubes assemblies, to the respective onboard tanks. However, this process of installing and uninstalling screw caps and inserting and removing dip tube assemblies into/from bulk solution containers is messy and tedious. Also, some automated diagnostic analyzers include multiple onboard tanks for storing different liquids. Thus, there may be multiple dip tube assemblies for the onboard tanks, where each of the dip tube assemblies corresponds to a certain onboard tank. Therefore, it can be imperative to connect the correct dip tube to the correct container of liquid. Otherwise, the wrong liquid can be mistakenly pumped into the wrong onboard tank, thereby compromising the integrity of the analysis procedures.

Some known container connection assemblies receive a liquid container in an upside down orientation and include a piercing probe that is inserted into the container to drain the contents. However, the piercing probes are exposed and can be dangerous to operators who are constantly inserting containers into the connection assemblies. Further, these connection assemblies can mistakenly receive the wrong containers having the wrong liquid and, thus, they also ultimately suffer from the above drawbacks.

BRIEF DESCRIPTION OF THE DRAWINGS

FIGS. 2A, 2B and 2C illustrate example caps having example key rings for mating with the example cradle of FIG. 1, which enable the example container of FIG. 1 to be inserted into the example cradle and drained.

FIG. 14A illustrates an example button of one of the example cradles being illuminated. FIG. 14B illustrates the example release button of FIG. 14A being depressed to release the corresponding container. FIG. 14C illustrates the example container of FIG. 14B being removed from the example cradle.

Figure 1:
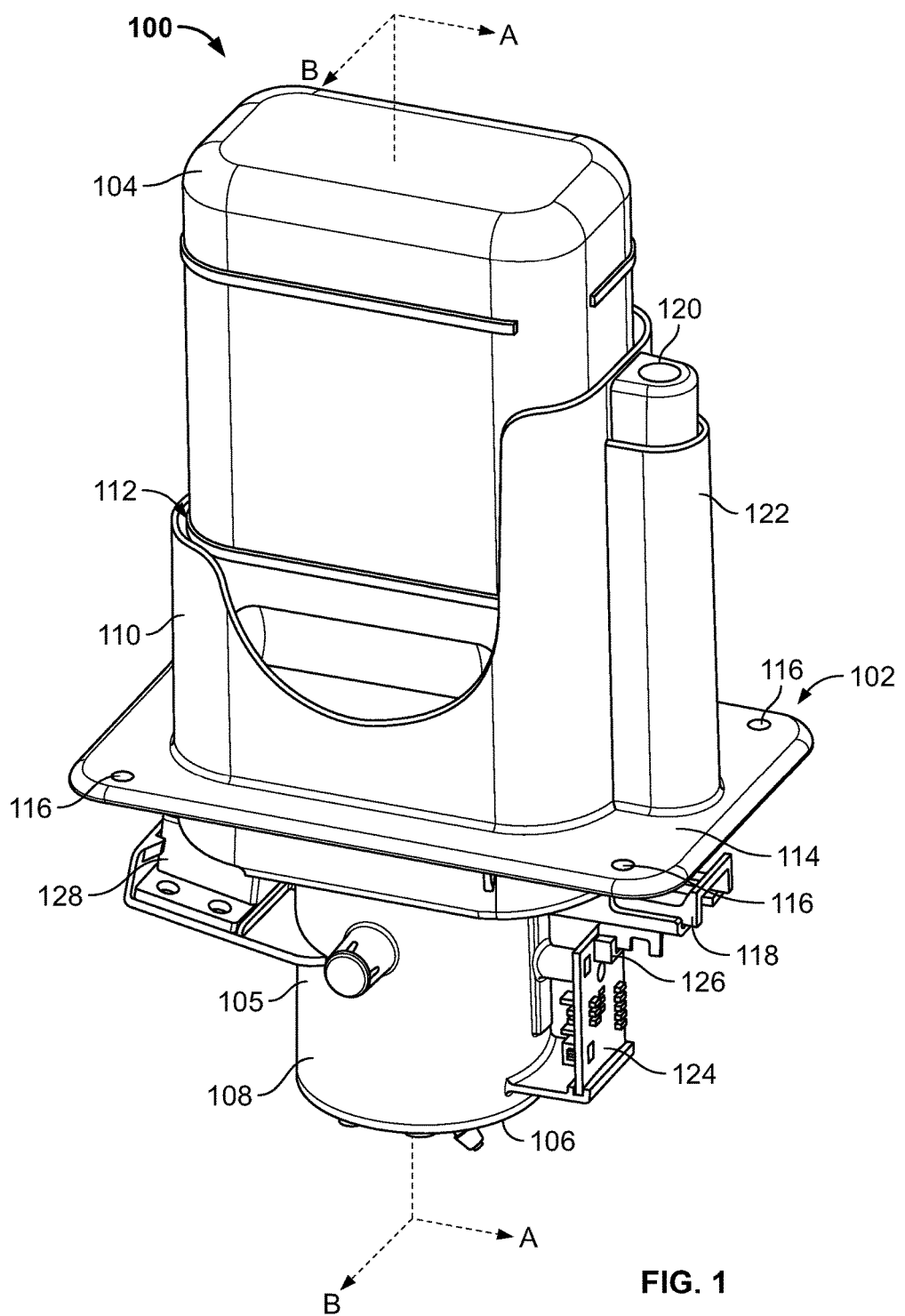
FIG. 1 is a perspective view of an example container inserted into an example cradle for draining the contents of the container and constructed in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

DETAILED DESCRIPTION

Automated diagnostic instruments or analyzers typically have one or more onboard tanks for storing (e.g., housing) bulk solutions or liquids (e.g., diluents, triggers, wash liquids, etc.) that are used during diagnostic analysis procedures. The tanks are often located within a chassis or body of the automated analyzers. To refill or replenish the onboard tanks, individual bottles or containers of bulk liquids are fluidly connected to the onboard tanks and the contents thereof are pumped into the onboard tanks. The containers are equipped with screw caps and dip tube assemblies are connected to the containers. However, removing the caps from the bulk liquid/solution containers, installing screw caps and changing dip tube assemblies is messy and cumbersome. Additionally, the dip tube assemblies are often not capable of aspirating all of the contents of the containers. Thus, when changing a bulk solution container, a small amount of liquid solution is often discarded, which, over time, can result in wasted solutions and increased costs. Further, some diagnostic analyzers have multiple onboard tanks. Therefore, there are multiple fluid lines coupling to each of the onboard tanks. As such, it is imperative that the correct refill container is coupled to the correct fluid line. Otherwise, the wrong liquid may be inadvertently supplied to the wrong onboard tank, thereby compromising the integrity of the diagnostic tests.

Disclosed herein are example cradle apparatus for receiving containers of solution or liquid and draining or pumping the liquid therein to another location (e.g., an onboard tank of a diagnostic analyzer). The example cradles have a unique sliding lock that allows only containers having matching key caps to be inserted into the cradle and drained. Therefore, unlike the dip tube assemblies describe above, the example cradles may only receive the correct or desired containers having the appropriate liquid therein, thereby reducing the chance of connecting the wrong container to the wrong fluid line. In some examples, multiple ones of the example cradles may be implemented, and each may be fluidly coupled to a corresponding tank. Each of the cradles may have a different key slot in the corresponding sliding lock, so that only containers with the matching key ring can be plugged into the cradles and emptied.

In some examples disclosed herein, a bulk liquid/solution container is inserted into a corresponding cradle upside down and, once inserted, a piercing probe punctures a cap on the container. The probe is fluidly connected to a barb on the bottom of the cradle, where a hose or tube may be connected to fluidly couple the probe to another location, such as an onboard storage tank. The cap has a septum and a specific key ring. The cap may be threadably coupled to the container. When the container is inserted upside down into the cradle, the cap engages a sliding lock that is disposed within a housing of the cradle. The sliding lock is located above a tip of the probe and is locked in place by one or more lockouts. If the cap has the correct key ring, the key ring fits into a key slot in the sliding lock, which engages a trigger that releases the lockouts and enables the sliding lock to move. More specifically, as the container is pushed down into the cradle, the key ring pushes the trigger downward, and beveled edges of the trigger slide against the lockouts and force the lock-out sliders outward. As the sliding lock moves downward, the probe, which is stationary, pierces the septum and extends into the container (e.g., to make a fluid connection in a system). The contents of the container can be drained or emptied through the probe. In some examples, the cradle includes a second probe that provides a vent (e.g., positive pressure) as the liquid is drained to prevent a vacuum from forming in the container.

In some examples, once the container is fully inserted into the cradle, a latch secures the container in position. The latch engages a lip on the cap after the cap has been pushed past the latch. To release the latch, an operator may push or depress a release button (such as for example, a release actuator, an eject button, and/or any other suitable release mechanism) that causes the latch to release the cap of the container. One or more springs may be disposed in the housing of the cradle to bias the sliding lock upwards. Therefore, when the latch is released, the container may be ejected from the housing of the cradle. Thus, the example cradles provide a simpler way to fluidly connect and disconnect a container to a fluid system.

If a container not having the correct cap (e.g., the correct key ring) is inserted into the cradle, the cap cannot engage the trigger to release the lockouts. As a result, the lockouts prevent the sliding lock from moving and, thus, prevent the container from being pierced by the probe and drained. In some examples, the cradle includes a sensor (such as for example, an integral sensor, a capacitive sensor, and/or any other suitable sensor) for detecting a level of liquid within the container. In some examples, the cradle includes a sensor for detecting when the latch is fully engaged (i.e., when the container is fully inserted). In some examples, the cradle may include one or more lights or other indicators to indicate different states of the cradle. For example, when the container is pushed all the way in and the latch is engaged, a light (e.g., a green light) may illuminate the release button (e.g., which may be transparent or semi-transparent). If the container is not fully inserted, another light (e.g., a yellow light) may illuminate the release button. In some examples, when the container is empty or low on liquid, another light (e.g., a red light) may illuminate the release button.

The example cradles disclosed herein are described in connection with bulk solution or liquid for use in an automated diagnostic analyzer (e.g., an immunoassay (IA) analyzer or a clinical chemistry (CC) analyzer). However, the example cradles may be used in any application where liquid is to transferred from a container to another location.

An example apparatus disclosed herein includes a housing having a bottom wall, a side wall and an open top. The housing is to receive a container having liquid to be used in an automated diagnostic analyzer. The example apparatus includes a probe extending upward from the bottom wall toward the open top. The probe is to drain the liquid from the container when the probe is inserted into the container. The example apparatus also includes a sliding lock slidably disposed within the housing. The sliding lock includes an engagement surface, an opening in the engagement surface to receive the probe therethrough when the sliding lock is moved from a first position in which the engagement surface is above a tip of the probe to a second position in which the engagement surface is below the tip of the probe, and a key slot in the engagement surface. The example apparatus includes a lockout located below the engagement surface of the sliding lock releasably coupled to the sliding lock. The lockout is movable between a locked position in which the sliding lock is prevented from moving in the housing and an unlocked position in which the sliding lock is movable in the housing. The key slot is to receive a key of the container that is inserted into the housing to move the lockout from the locked position to the unlocked position.

In some examples, the apparatus includes a trigger that is disposed below the engagement surface of the sliding lock. The trigger is engageable with the key to move the trigger toward the bottom wall of the cradle to move the lockout to the unlocked position.

In some examples, the trigger is movable along a first axis and the lockout is movable along a second axis that is perpendicular to the first axis. In some such examples, the trigger has a beveled surface that is to engage the lockout when the trigger moves toward the bottom wall of the housing to move the lockout along the second axis.

In some examples, the key slot is a ring-shaped slot. In some such examples, the key is a ring-shaped protrusion that matches the ring-shaped slot.

In some examples, the apparatus includes a resilient member to bias the sliding lock away from the bottom wall of the housing. In some examples, the apparatus includes a latch to engage a rim on the container to releasably secure the container in the housing when the container is inserted into the housing. In some such examples, the apparatus includes a release actuator to release the latch. The release actuator has a light that is to illuminate when the container is fully inserted into the housing.

In some examples, the housing is to receive the container in an upside-down orientation. In some examples, the apparatus includes a barb disposed on an outer surface of the bottom wall to fluidly couple an inner passage of the probe to a tube coupled to the barb.

Another example apparatus disclosed herein includes a housing having a bottom wall, a side wall and an open top. The housing is to receive a container having liquid to be used in an automated diagnostic analyzer. The example apparatus includes a probe extending upward from the bottom wall toward the open top. The probe is to drain the liquid from the container when the probe is inserted into the container. The example apparatus also includes a sliding lock slidably disposed within the housing. The sliding lock includes an engagement surface, an opening in the engagement surface to receive the probe therethrough when the sliding lock is moved from a first position in which the engagement surface is above a tip of the probe to a second position in which the engagement surface is below the tip of the probe, and a key slot in the engagement surface. The example apparatus includes a lockout releasably coupled to the sliding lock to prevent movement of the sliding lock when the lockout is in a locked position. The example apparatus also includes a trigger disposed below the engagement surface of the sliding lock. The trigger is engageable with a key of the container inserted into the key slot to move the trigger toward the bottom wall of the housing to move the lockout to an unlocked position in which the sliding lock is movable in the housing.

In some examples, the sliding lock and the trigger are moveable along the same axis. In some examples, the trigger includes a second opening to receive the probe therethrough when the trigger is moved toward the bottom wall of the housing. In some such examples, the second opening of the trigger is concentric with and outside of the first opening of the sliding lock.

In some examples, the apparatus includes a first spring to bias the trigger away from the bottom wall of the housing. In some such examples, the apparatus includes a second spring to bias the sliding lock away from the bottom wall of the housing.

In some examples, the trigger is movable along a first axis and the lockout is movable along a second axis, the second axis perpendicular to the first axis. In some examples, the trigger includes a beveled surface that is to engage the lockout when the trigger is activated to move the lockout in a direction that is perpendicular to the movement of the trigger.

Another example apparatus disclosed herein includes a housing to receive a container having liquid to be used in an automated diagnostic analyzer. The housing has a bottom wall, a side wall and an open top. The example apparatus includes a probe extending upward from the bottom wall toward the open top. The probe is to drain the liquid from the container when the probe is inserted into the container. The example apparatus also includes a sliding lock slidably disposed within the housing. The sliding lock includes an engagement surface disposed above the probe, an opening in the engagement surface to receive the probe therethrough when the sliding lock is moved toward the bottom wall of the housing, and a key slot. The sliding lock is operable between a locked state in which movement of the sliding lock is prevented and an unlocked state in which the sliding lock is movable. The sliding lock is switched to the unlocked state when a cap of the container includes a key corresponding to the key slot engages the key slot.

An example method is disclosed herein that includes inserting a container with a cap having a key ring into a cradle. The cradle includes a housing, a probe disposed in the housing, a sliding lock slidably disposed in the housing, the sliding lock having (1) an engagement surface, (2) an opening in the engagement surface to receive the probe therethrough when the sliding lock is moved from a first position in which the engagement surface is above a tip of the probe to a second position in which the engagement surface is below the tip of the probe, and (3) a key slot in the engagement surface, and a lockout located below the engagement surface of the sliding lock releasably coupled to the sliding lock. The example method includes moving the container into the cradle. If the key ring matches the key slot, the lockout is moved between a locked position in which the sliding lock is prevented from moving in the housing and an unlocked position in which the sliding lock is movable in the housing to the second position. The example method also includes coupling the container in the cradle and draining the contents of the container via the probe.

In some examples, the container is inverted when the container is inserted into the cradle. In some examples, the cradle includes a latch that is movable between a non-engaged position in which the container is moveable out of the cradle and an engaged position in which the container is coupled in the cradle. In some such examples, the method includes determining, via a latch position sensor, whether the latch is in the non-engaged position or the engaged position. In some such examples, the method also includes determining, via a liquid level sensor, a level of liquid in the container. In some such examples, the method includes actuating a first indicator when the latch is determined to be in the engaged position. In some such examples, the method also includes actuating a second indicator when the level of liquid in the container is determined to be below a threshold. In some examples, the first indicator is a first color light and the second indicator is a second color light different than the first color light in some examples, the first indicator and the second indicator are disposed within a release button of the cradle.

FIG. 1 illustrates an example bulk solution system 100 in which an example cradle 102 is implemented to receive a bottle or container 104 and drain the liquid contents thereof. The contents may be, for example, a reagent, a wash solution, a trigger, a diluent and/or any other solution or liquid for use in an automated diagnostic analyzer. The example container 104 may be any volume desired (e.g., 1 liter). In the illustrated example, the cradle 102 includes a body or housing 105 having a bottom wall 106 and a side wall 108 that define an opening (e.g., an open top) to receive a top of the container 104 (as disclosed in further detail herein). When the container 104 is fully inserted into the cradle 102, the contents of the container 104 can be drained or removed via one or more openings (e.g., through-holes, apertures) in the bottom wall 106 (disclosed in further detail herein). In the illustrated example, the cradle 102 includes a container holder 110 (e.g., a molding) that defines an opening 112 that is shaped to receive the container 104 and support the container 104 in an upside down or inverted orientation. In the illustrated example, the container 104 has a substantially rectangular cross-section with curved edges. However, in other examples, the container 104 may have a circular shaped cross-section or any other shaped cross-section. In the illustrated example, the cradle 102 has a mounting plate 114 with one or more holes 116 that may be used to mount the cradle 102 to another structure (e.g., to an automated diagnostic analyzer, to a drawer of an analyzer, etc.).

In the illustrated example of FIG. 1, the cradle 102 includes a latch 118 and a release button 120 (e.g., an eject button, a release actuator). When the container 102 is fully inserted into the cradle 102, the latch 118 secures the container 104 to the cradle 102 to prevent the container 104 from being removed (e.g., inadvertently) from the cradle 102. To release the container 104, the release button 120 may be depressed. The release button 120 engages the latch 118 and thereby releases the latch 118 from the container 104. The release button 120 is disposed within a release button housing 122 along a side of the container holder 110. In the illustrated example, the cradle 120 includes a circuit board 124 (e.g., a processor, a printable circuit board (PCB), a microchip, etc.), a latch position sensor 126 (e.g., an encoder, an optical sensor) and a liquid level sensor 128 (e.g., an integral sensor, a capacitive sensor), which are disclosed in further detail herein.

In the illustrated example, the cradle 102 only accepts containers having a cap or top with a particular key ring that matches a key slot in the cradle 102 (disclosed in further detail herein). FIGS. 2A, 2B and 2C illustrate example caps 200 that may be used with the container 104 (FIG. 1). Each of the caps 200 has a key ring 202 that matches a key slot in a corresponding cradle. In the illustrated examples, the key rings 200 are in the shape of circles that extend from the caps 200. The key ring 202 of the cap 200 in FIG. 2A has relatively small diameter compared to the diameters of the key rings 202 of the caps 200 in FIGS. 2B and 2C. The key ring 202 of the cap 200 in FIG. 2C has the largest diameter, and the key ring 202 of the cap 200 in FIG. 2B has a diameter having a dimension between the key rings 202 of the caps 200 in FIGS. 2A and 2C. The different caps 200 of FIGS. 2A-2C may correspond to different containers having different liquids. Each of the caps 200 may interact with respective cradles having a matching key slot. Therefore, if one of the caps 200 is inserted into the wrong cradle, the key ring 202 may not have the correct diameter key to be received by the cradle and drained. In the illustrated examples, three different sized key rings 202 are illustrated, where each of the key rings 202 is to be used with a particular type of container of liquid. However, it is to be understood that many more caps having different diameter key rings could be implemented. Additionally or alternatively, other caps having different shaped key rings may also be implemented (e.g., square, rectangular, etc.).

Figure 3A:
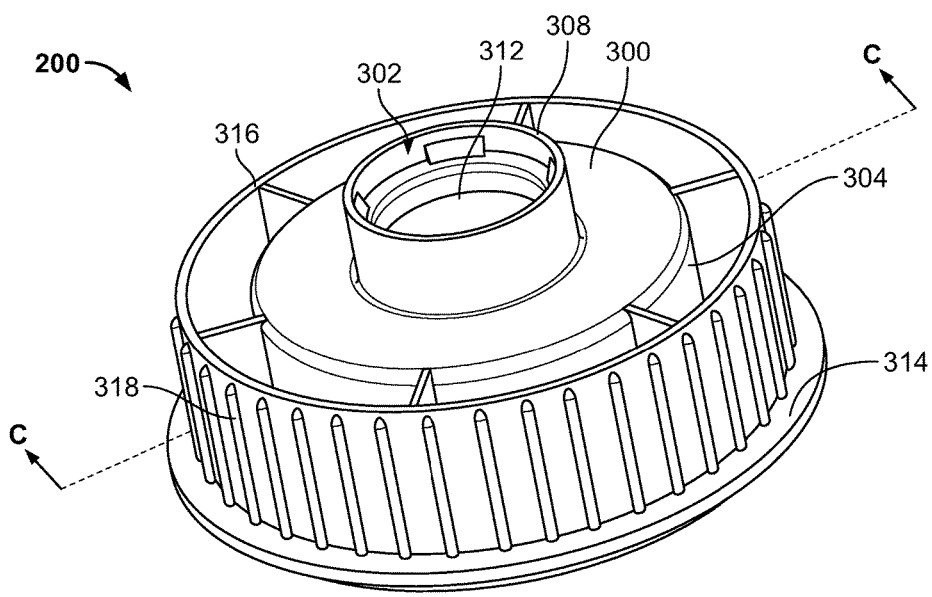
FIG. 3A is a perspective view of one of the example caps of FIGS. 2A-2C shown without the example key ring.
Figure 3B:
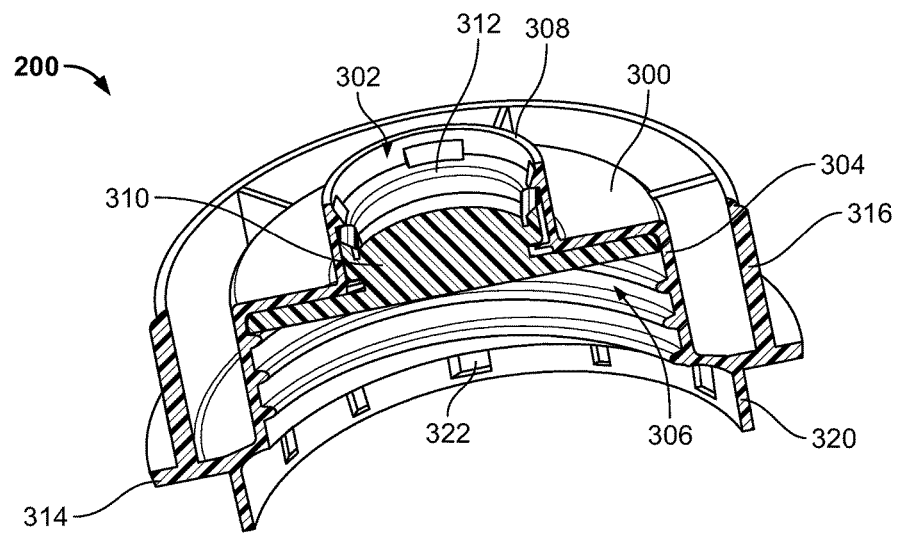
FIG. 3B is a cross-sectional view of the example cap of FIG. 3A taken along line C-C of FIG. 3A.

FIG. 3A illustrates a perspective view of one of the caps 200, and FIG. 3B illustrates a cross-sectional view of the cap 200 taken along line C-C of FIG. 3A. In the illustrated example of FIGS. 3A and 3B, the key ring 200 (FIGS. 2A-2C) has been removed for clarity. The cap 200 has a lid or surface 300 with an opening 302 (e.g., an aperture, a hole, a channel) therethrough. A side wall 304 with internal threads 306 extends from one side of the lid 300, and an annular lip or rim 308 extends from the other side of the lid 300. The cap 200 may be screwed onto a container (e.g., the container 104 of FIG. 1) via the threads 306. In the illustrated example, the cap 200 includes a septum 310 that is disposed within the opening 302 and is held in place by a snap ring 312. The septum 310 may be made of any suitable material, such as silicon or rubber. The snap ring 312 is wedged (e.g., via force fit, via a tab) between an inside of the rim 308 and the septum 310. In the examples illustrated in FIGS. 2A-2C, the rim is illustrated as a plurality of individual extensions. In other examples, such as the example illustrated in FIGS. 3A and 3B, the rim is a continuous wall extending from the lid 300.

In the illustrated example, the cap 200 has a wall or flange 314 extending outward from the side wall 304. The flange 314 is substantially parallel to the lid 300. An outer wall 316 extends upward from the flange 314 in a direction that is parallel to the side wall 304. The outer wall 316 has a plurality of ribs 318 that allow a user to grip the cap 200 (e.g., when tightening or loosening the cap 200 on a container). A lower side wall 320 extends downward from the flange 314 and has a plurality of ratchet groves 322, which enable the cap 200 to be ratcheted tightly onto a container and prevent the cap 200 from loosening from container. The cap 200 may be constructed of any suitable material such as, for example, polypropylene.

Figure 4:
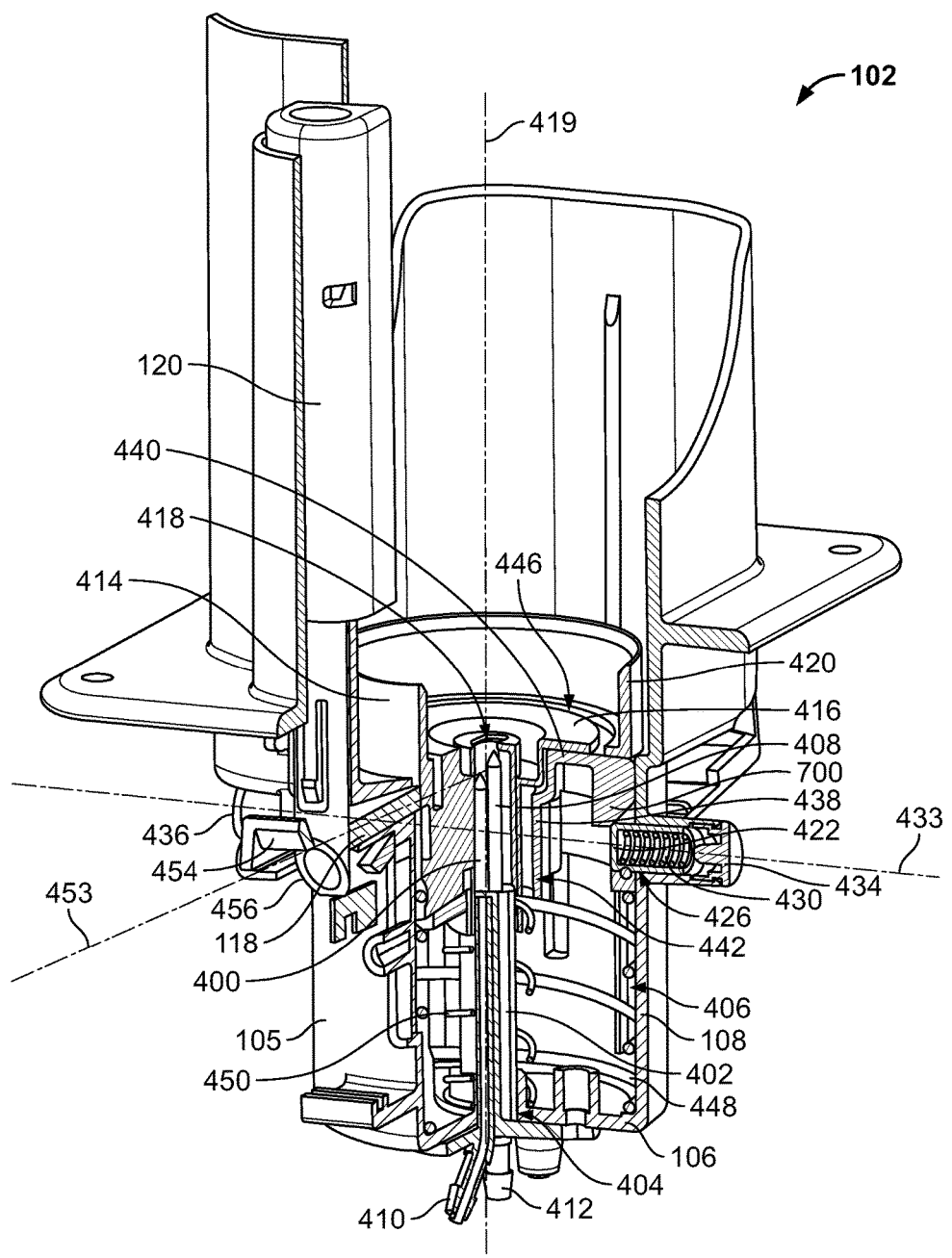
FIG. 4 is a partially cross-sectioned view of the example cradle of FIG. 1 without the example container.
Figure 5:
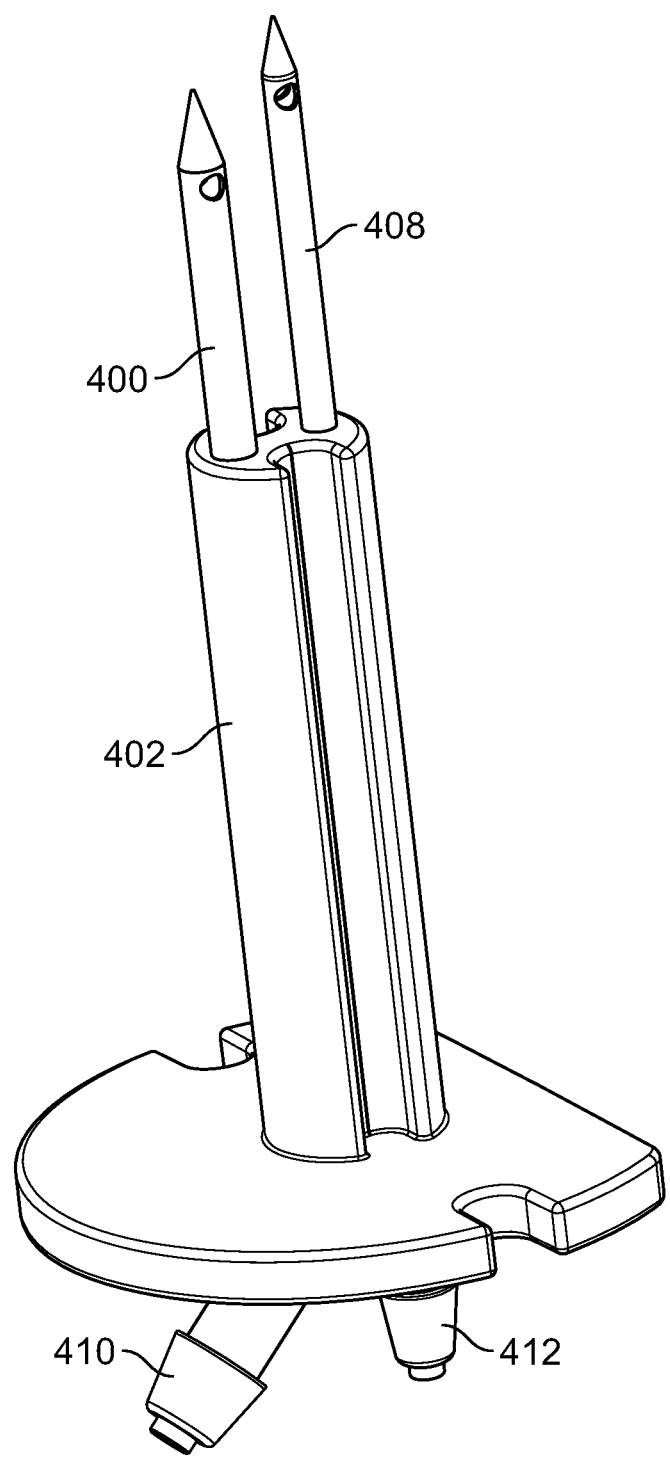
FIG. 5 is a perspective view of an example probe mount that may be implemented with the example cradle of FIG. 1.

FIG. 4 illustrates a partially cross-sectioned view of the example cradle 102. The container 104 has been removed for clarity. To drain the contents of a container (e.g., the container 104 of FIG. 1), the cradle 102 has a piercing drain probe 400 (e.g., a needle) that may puncture a cap and/or a septum on a cap (e.g., the cap 200 of FIG. 3A) and be inserted into a container. The drain probe 400 is coupled to a probe mount 402 (e.g., an insert molded probe assembly) that extends through an opening 404 in the bottom wall 106 of the housing 105. The drain probe 400 extends or projects upward and away from the bottom wall 106 within an opening 406 defined by the bottom wall 106 and the side wall 108. In the illustrated example, the cradle 102 includes a vent probe 408 that is disposed adjacent the drain probe 400. The vent probe 408 is to vent the inside of a container to prevent a vacuum from forming inside of the container while the contents are drained. The vent probe 408 is coupled to the probe mount 402. The probe mount 402 includes passages that couple the probes 400, 408 to first and second barbs 410, 412 (e.g., nipples, fittings, adaptors, barbed connectors, etc.), respectively, on an outside of the bottom wall 106. Hoses or tubes may be coupled to the first and second barbs 410, 412 to fluidly couple the drain probe 400 and/or the vent probe 408 to a desired location (e.g., to an onboard tank). The example probe mount 402 is illustrated in FIG. 5, which illustrates the drain probe 400, the vent probe 408, and the first and second barbs 410, 412.

Figure 6A:
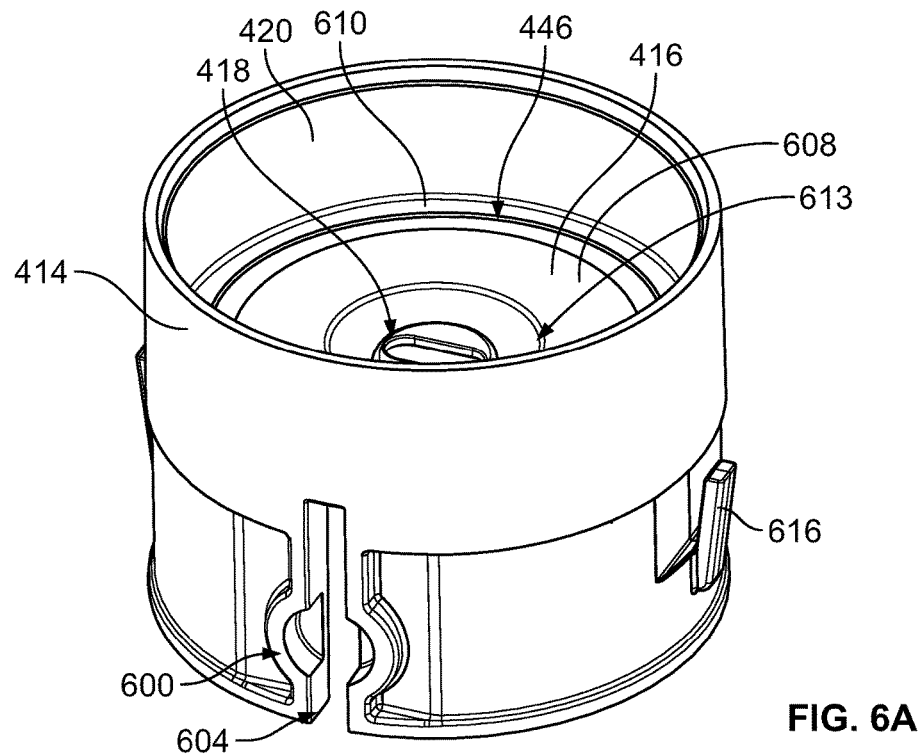
FIG. 6A is a top perspective view of an example sliding lock that may be implemented with the example cradle of FIG. 1.
Figure 6B:
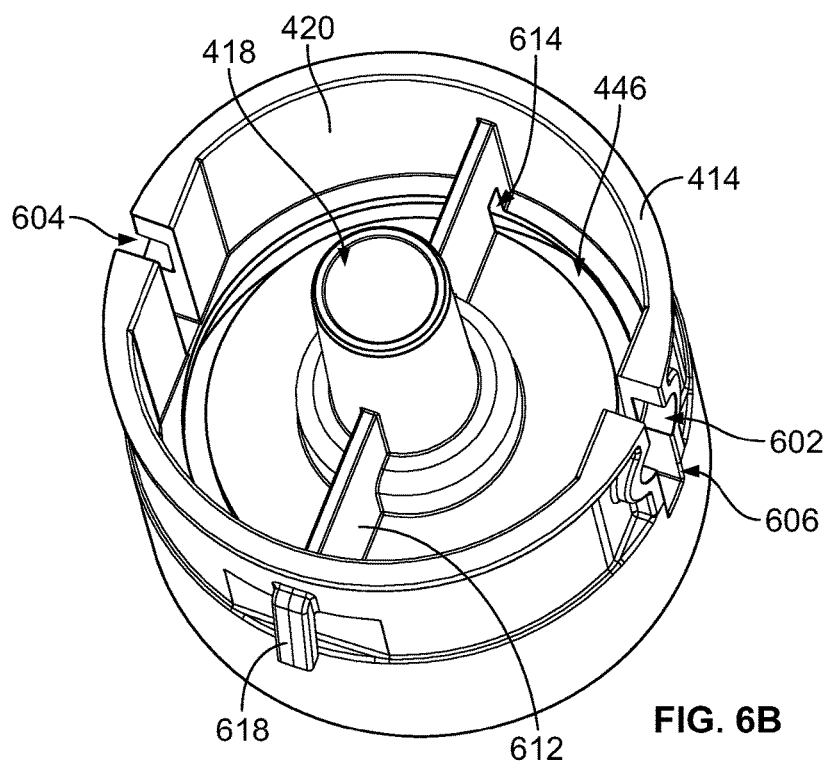
FIG. 6B is a bottom perspective view of the example sliding lock of FIG. 6A.

Referring to FIG. 4, to prevent unintended containers from being inserted into the housing 105 and pierced and drained, the example cradle 102 includes a sliding lock 414 that is slidably disposed within the opening 406 of the housing 105. FIG. 6A illustrates a top perspective view of the sliding lock 414 and FIG. 6B illustrates a bottom perspective view of the sliding lock 414, which are numbered in accordance with the disclosure herein. The sliding lock 414 has an engagement surface 416 that is to receive a cap or top of a container (e.g., contacted by a cap or top of a container). The engagement surface 416 has an opening 418 to receive the probes 400, 408 when the sliding lock 414 is moved downward or toward the bottom wall 106 (e.g., from a first position to a second position). The sliding lock 414 is movable along a first axis 419 (e.g., a longitudinal axis of the housing 105). When the sliding lock 414 is moved downward (e.g., when a container having a matching key ring is inserted), the probes 400, 408 extend through the opening 418 to pierce a cap and/or septum of a container. In the illustrated example of FIG. 4, the sliding lock 414 is a first or unengaged position where the probes 400, 408 are disposed below the engagement surface 416. As such an operator cannot accidently poke himself/herself. The sliding lock 414 is movable from the first position to a second position in which the engagement surface 416 is below the tip of the probes 400, 408 (as disclosed in further detail herein).

In the illustrated example, the sliding lock 414 has an outer wall 420 that is in the shape of a cylinder or sleeve. The outer wall 420 matches the shape of the opening 406 as defined by the side wall 106 of the housing 105. However, in other examples the outer wall 420 of the sliding lock 414 may be shaped differently. For example, the outer wall 420 may be substantially a square or triangular shape.

Figure 8:
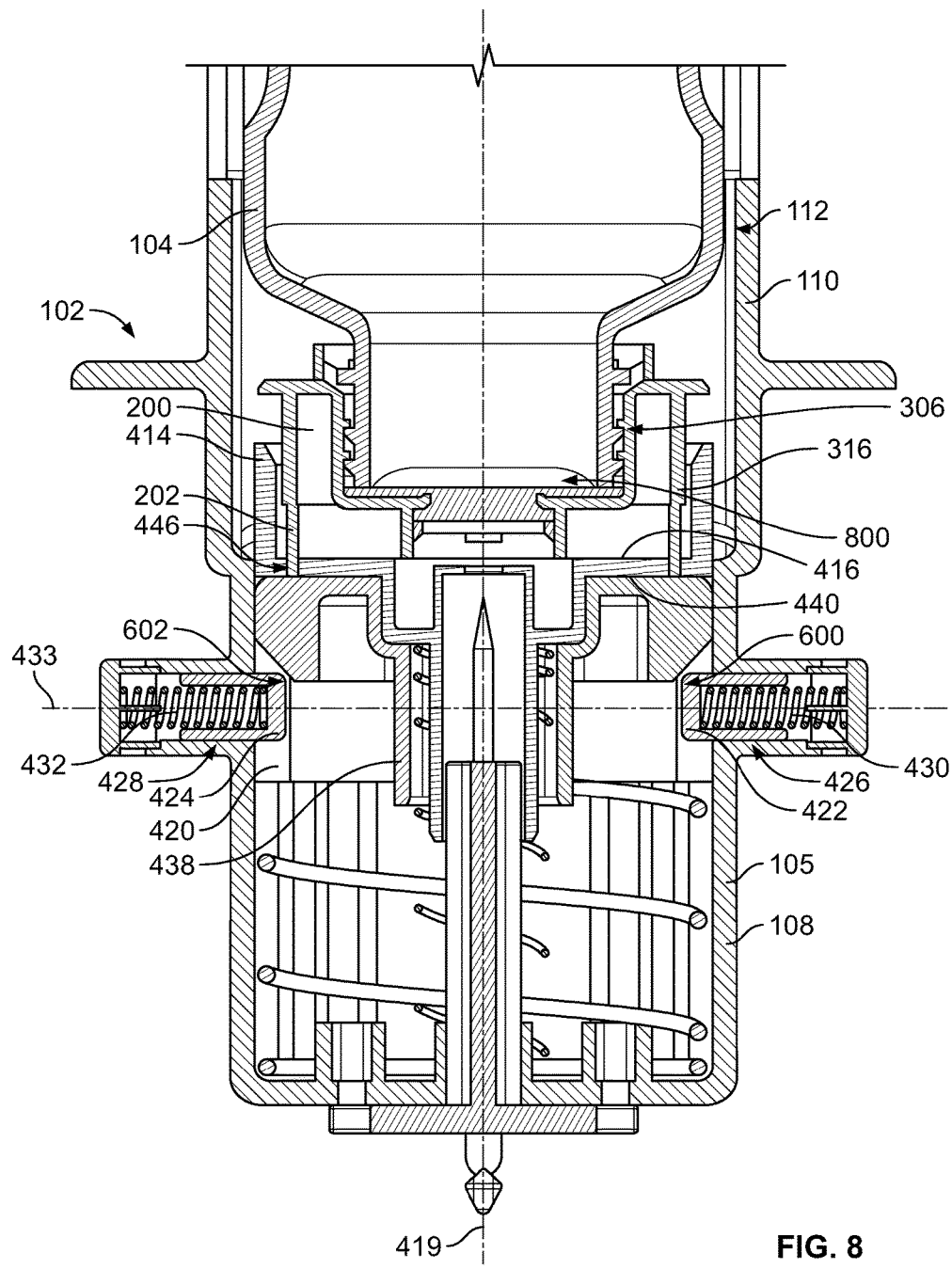
FIG. 8 is a cross-sectional view of the example container and the example cradle of FIG. 1 taken along line A-A of FIG. 1, where the example container is in a first position in which the example container is not fully inserted into the example cradle. The example cap of FIG. 2C is employed on the example container and is engaging the example sliding lock of FIGS. 6A and 6B.
Figure 9:
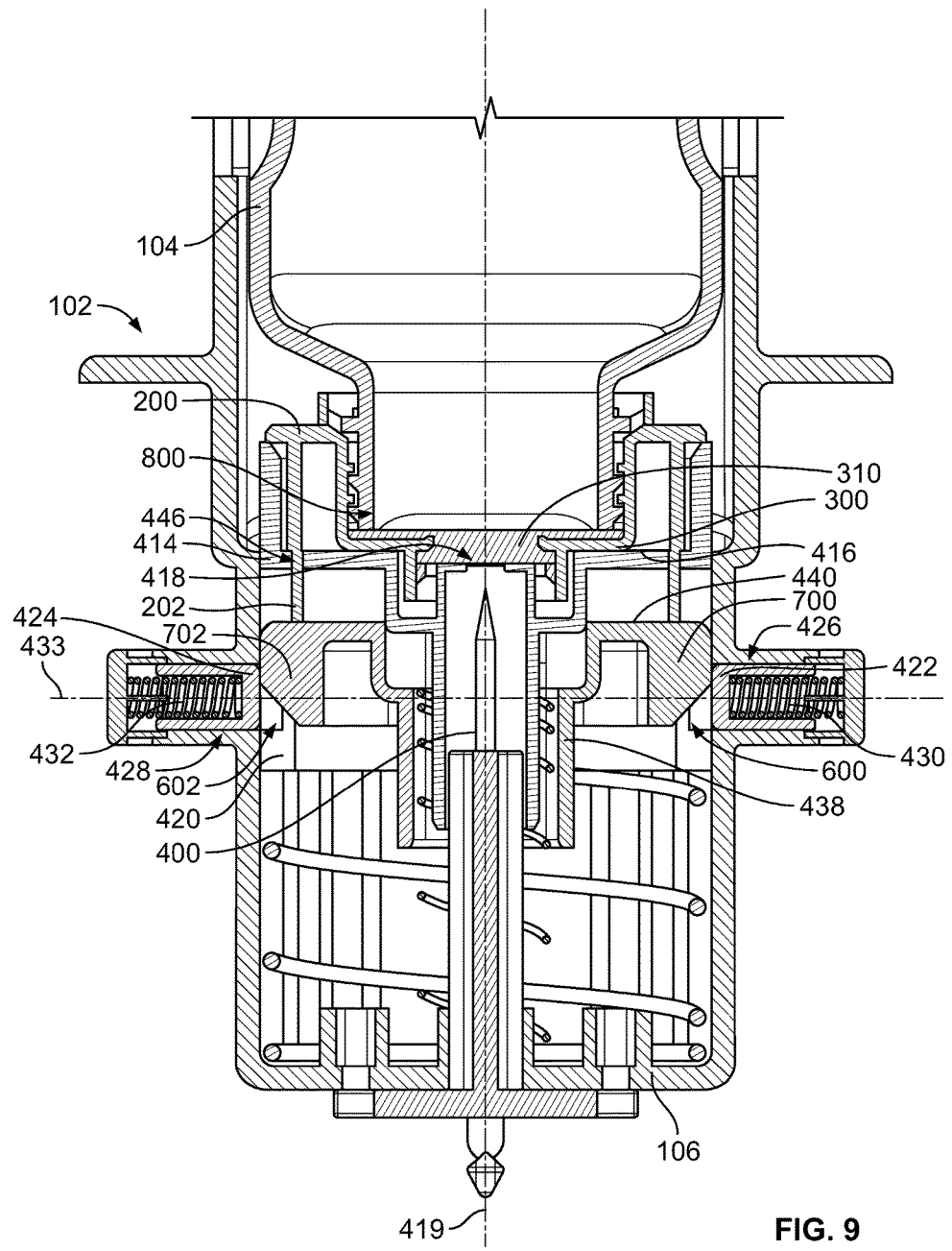
FIG. 9 is another cross-sectional view of the example container and the example cradle of FIG. 1 taken along line A-A of FIG. 1, where the example container is in a second position in which the example container is partially inserted into the example cradle. The example container is pushed down into the example cradle and the example sliding lock is slid into the example cradle.

To prevent the sliding lock 414 from being pushed down towards the bottom wall 106 by an undesired container (e.g., a container with the wrong liquid), the cradle 102 includes a first lockout 422 (e.g., a locking button, a lockout slider) and a second lockout 424 (FIGS. 8 and 9), which are disposed in the side wall 108 of the housing 105 and extend into the outer wall 420 of the sliding lock 414. The first and second lockouts 422, 424 prevent the sliding lock 414 from moving toward the bottom wall 106, which would thereby enable the probes 400, 408 to extend through the sliding lock 414 and pierce a cap and/or a septum of a container. The first and second lockouts 422, 424 are movable between a locked position (as illustrated in FIGS. 4 and 8) and an unlocked position (as illustrated in FIG. 9). The first and second lockouts 422, 424 are disposed within respective openings 426, 428 (seen more clearly in FIGS. 8 and 9) in the side wall 108. The first and second lockouts 422, 424 are biased via respective first and second springs 430, 432 (seen more clearly in FIGS. 8 and 9) toward a center of the cradle 102 along a second axis 433, which is perpendicular to the first axis 419 along which the sliding lock 416 moves. Retaining caps 434, 436 (e.g., retaining buttons) are removably coupled to the respective openings 426, 428 (e.g., to enable access to the first and second lockouts 422, 424 and the first and second springs 430, 432). In the locked position, the first and second lockouts 422, 424 extend into (e.g., are inserted into) respective first and second notches 600, 602 (FIGS. 6A and 6B) in the outer wall 420 of the sliding lock 414. As a result, the sliding lock 414 is prevented from moving upward or downward and, thus, the probes 400, 408 cannot be exposed through the opening 418.

In the illustrated example of FIG. 4, the first and second lockouts 422, 424 are located opposite of each other on the side wall 108. However, in other examples, the first and second lockouts 422, 424 are disposed in other locations (e.g., closer to each other) and/or at different lengths or heights along the side wall 108. In some examples, only one lockout is implemented. In other examples, more than two lockouts are implemented.

Figure 7A:
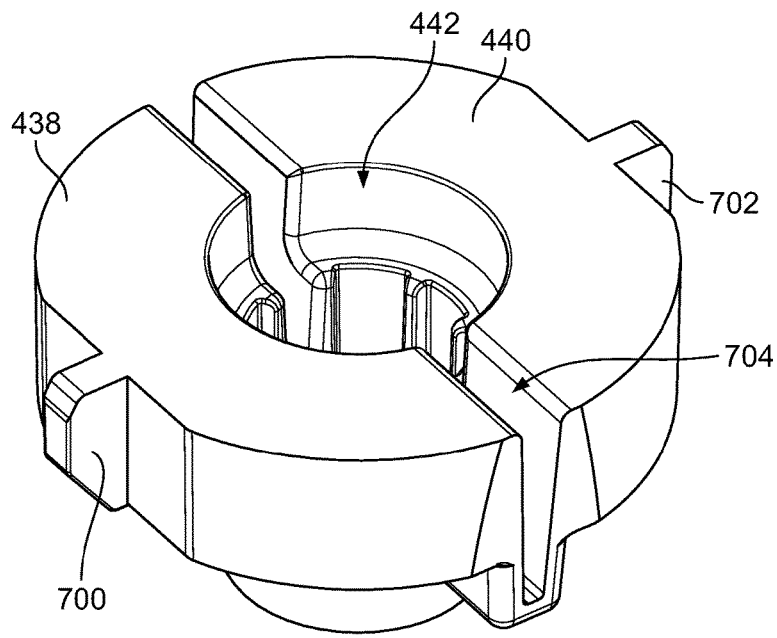
FIG. 7A is a top perspective view of an example trigger that may be implemented with the example cradle of FIG. 1.
Figure 7B:
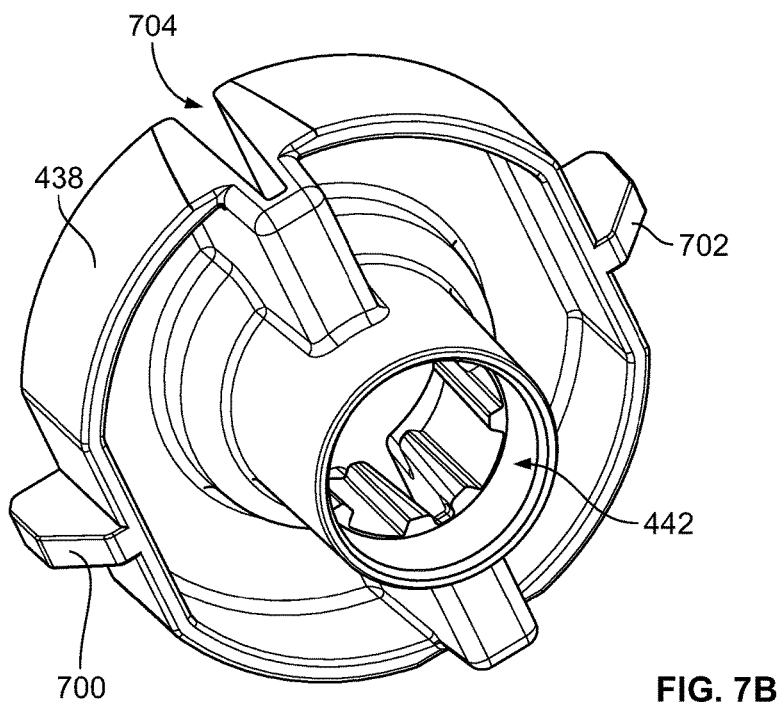
FIG. 7B is a bottom perspective view of the example trigger of FIG. 7A.

To release the first and second lockouts 422, 424, the cradle 102 includes a trigger 438 that is disposed between the sliding lock 414 and the bottom wall 106 (e.g., beneath the engagement surface 416 of the sliding lock 414). FIG. 7A illustrates a top perspective view of the trigger 438 and FIG. 7B illustrates a bottom perspective view of the trigger 438, which are numbered in accordance with the disclosure herein. The trigger 438 has an engagement surface 440 that is parallel to the engagement surface 416 of the sliding lock 414. The engagement surface 440 of the trigger 438 has an opening 442 that is concentric with the opening 418 of the sliding lock 414. As illustrated in FIG. 4, the trigger 438 is movable along the first axis 419. As illustrated in FIGS. 7A and 7B, the trigger 438 has a first tab 700 with a beveled or angled surface and a second tab 702 with a beveled or angled surface. In the illustrated example, the first and second tabs 700, 702 extend outward from the engagement surface 440. As illustrated in FIGS. 6A and 6B, the sliding lock 414 has a first slot 604 and a second slot 606 that receive the respective first and second tabs 700, 702 of the trigger 438. The first and second slots 604, 604 intersect the first and second notches 600, 602, respectively. Therefore, when the trigger 438 is moved toward the bottom wall 106, the first and second tabs 700, 702 engage the respective first and second lockouts 422, 424 and force the first and second lockouts 422, 424 outward (e.g., along the second axis 433) such that the first and second lockouts 422, 424 are disengaged from the first and second notches 600, 602 in the outer wall 420 of the sliding lock 414. As a result, the sliding lock 414 is able to be moved downward toward the bottom wall 106.

To move the trigger 438 (which is disposed beneath the engagement surface 416 of the sliding lock 414) downward to disengage the first and second lockouts 422, 424, the sliding lock 414 has a key slot 446 in the engagement surface 416. The key slot 446 is an opening that has a shape corresponding to a particularly key ring of a cap. When a cap having a matching or corresponding key ring is inserted into the cradle 102, the key ring fits within the key slot 446 and engages the trigger 438 (e.g., the engagement surface 440 of the trigger 438) to move the trigger 438 toward the bottom wall 106 and, thus, release the first and second lockouts 422, 424 from the sliding lock 414. Once the first and second lockouts 422, 424 are disengaged, the sliding lock 414 is free to be pushed toward the bottom wall 106. As the sliding lock 414 is moved downward, the probes 400, 408 extend through the opening 418 and engage the cap of the container. In the illustrated example, the key slot 446 is a ring-shaped slot. However, in other examples, the key slot 446 may be any other shape (e.g., a triangle, a square, a star, etc.) and/or other size that corresponds to a particular key shape on a cap of a container.

As illustrated in FIGS. 6A and 6B, the key slot 446 divides the engagement surface 416 into an inner surface 608 and an outer surface 610. The inner and outer surface 608, 610 are coupled together via a support bar 612. The support bar 612 includes notches 614 at the intersection of the key slot 416 to accommodate a key ring when the key ring is inserted into the key slot 416, thereby enabling the key ring to engage the trigger 438. As illustrated in FIGS. 7A and 7B, the trigger 438 has a slot 704 in the engagement surface 440 to receive the support bar 612 when the trigger 438 is disposed below the sliding lock 414 (e.g., as illustrated in the position in FIG. 4). In the illustrated example of FIG. 6A, the engagement surface 416 of the sliding lock 414 includes a recess 613 to receive the rim 308 of the cap 200 (FIG. 3).

In the illustrated example of FIG. 4, the cradle 102 includes a first spring 448 (e.g., a resilient member, a return spring, and/or any other suitable biasing device) that is disposed between the bottom wall 106 and the sliding lock 414 to bias the sliding lock 414 upward and away from the bottom wall 106. The first spring 448 applies an upward forced to eject the bottle 104 from the cradle 102. In the illustrated example, the cradle 102 includes a second spring 450 that is disposed between the bottom wall 106 and the trigger 440 to bias the trigger 400 upward and away from the bottom wall 106. In other examples, other mechanisms may be used to bias the sliding lock 414 and/or the trigger 438.

To secure a container to the cradle 102 once a container is inserted into the cradle 102 and moved down so that the probes 400, 408 are disposed within the container, the latch 118 (e.g., a sliding latch, a lever, a trigger) is provided to engage a lip or rim on a cap of a container to prevent the container from being forced upward (e.g., via the first spring 448 and/or the second spring 450). The latch 118 moves along a third axis 453 (FIGS. 4 and 10) that is perpendicular to the first axis 419 along which the sliding lock 414 moves. The latch 118 has a beveled edge 454. When the release button 120 is pushed downward, a beveled edge 456 of the release button 120 engages the beveled edge 454 of the latch 118 and moves the latch 118 outward along the third axis 453 (e.g., away from a center of the cradle 102). As a result, the latch 118 releases the rim or lip of the cap and the container is free to be removed from the cradle 102 (e.g., via the force provided by the first and second springs 448, 450).

FIG. 8 illustrates a cross-sectional view of the cradle 102 and the container 104 of FIG. 1 (taken along line A-A of FIG. 1) when the container 104 is a first position and as the container 104 is inserted into the cradle 102. In the illustrated example, the container 104 is inverted upside down and placed into the opening 112 defined by the container holder 110. In the illustrated example, the cap 200 of FIG. 2C has been threaded onto an opening 800 (e.g., a mouth) of the container 104 (e.g., via the threads 306). As illustrated in the example of FIG. 8, the first and second lockouts 422, 424, which are disposed within the respective first and second openings 426, 428 of the wall 108, are biased inward toward a center of the cradle 102 via the respective first and second springs 430, 432. The first and second lockouts 422, 424 are movable along the second axis 433, which is perpendicular to the first axis 419 along which the sliding lock 414 moves. In the illustrated example, the first and second lockouts 422, 424 are in a locked or engaged position in which they are inserted into the respective first and second notches 600, 602 in the outer wall 420 of the sliding lock 414. As a result, the sliding lock 414 is prevented from moving upward or downward in the housing 105.

In the illustrated example, the cap 200 is the matching cap that enables the container 104 to be inserted into the cradle 102 to move the sliding lock 414. In particular, the key ring 202 of the cap 200 matches the shape of the corresponding key slot 446 in the engagement surface 416 of the sliding lock 414. Therefore, when the container 104 is pushed down into the cradle 102, the key ring 202 extends through the key slot 446 and engages the engagement surface 440 of the trigger 438. The outer wall 316 of the cap 200 is received by the outer wall 420 of the sliding lock 414 and aligns the cap 200 within the sliding lock 414.

FIG. 9 illustrates a cross-sectional view of the cradle 102 and the container 104 (also taken along line A-A of FIG. 1) when the container 104 is in a second position in which the container 104 is partially inserted into the cradle 102 (e.g., when the container 104 is pushed further down into the cradle 102 than the position of FIG. 8). As illustrated, the lid 300 of the cap 200 engages the engagement surface 416 of the sliding lock 414, and the key ring 202 is inserted through the key slot 446 and engages the engagement surface 440 of the trigger 438 to move the trigger 438 downward toward the bottom wall 106. The beveled surfaces of the first and second tabs 700, 702 of the trigger 438 engage the first and second lockouts 422, 424, respectively, and push the first and second lockouts 422, 424 outward (e.g., along the second axis 433) away from the first and second notches 600, 602 in the outer wall 420 of the sliding lock 414. As a result, the sliding lock 414 is free to move (e.g., with the trigger 438) downward toward the bottom wall 106 (e.g., along the first axis 419). As the container 104 and sliding lock 414 move downward toward the bottom wall 106, the probes 400, 408 (see FIG. 4) extend through the opening 418 in the sliding lock 414 and pierce the septum 310 in the cap 200 and extend into the opening 800 of the container 104. In some examples, a pump is activated that creates a suction in the drain probe 400 to actively remove the liquid contents of the container 104. In other examples, the contents of the container 104 may be drained via gravity (e.g., without the assistance of a pump).

Figure 10:
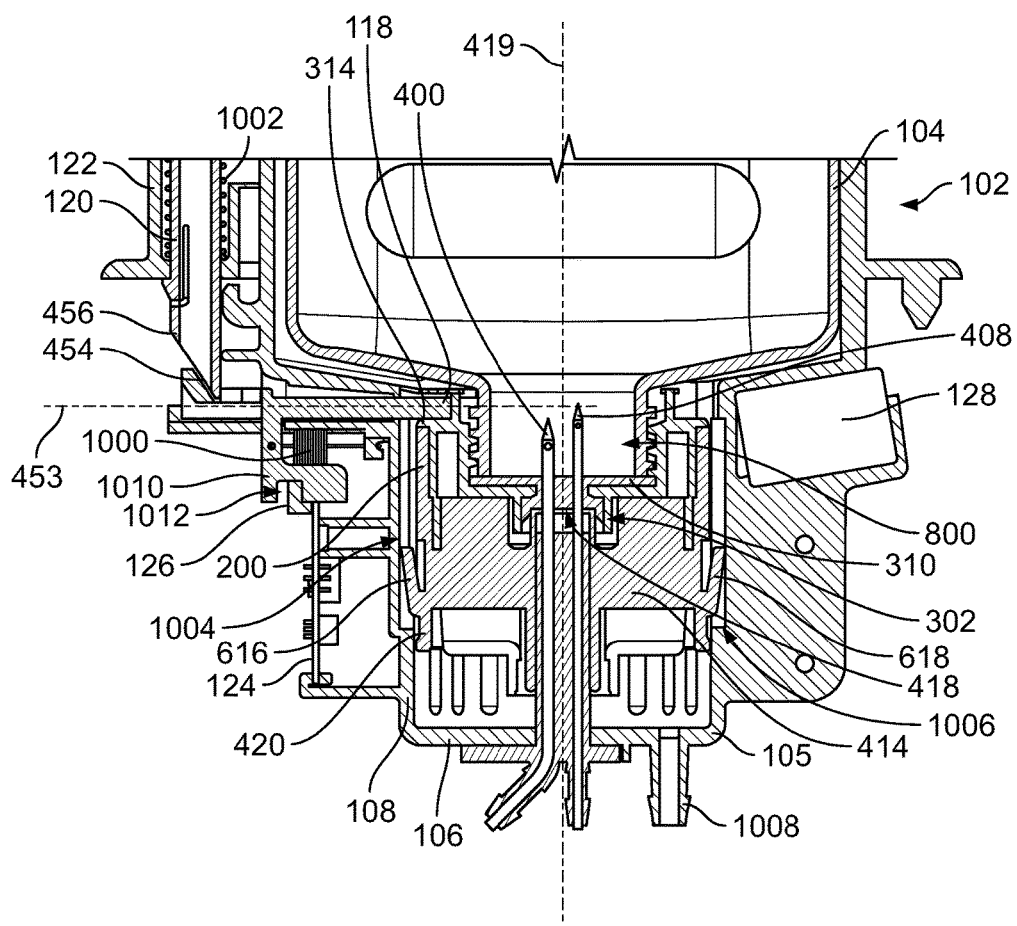
FIG. 10 is a cross-sectional view of the example cradle and the example container of FIG. 1 taken along line B-B of FIG. 1, where the example container is in a third position in which the example container is fully inserted into the example cradle and where the contents of the example container may be drained.

FIG. 10 illustrates a cross-sectional view of the cradle 102 and the container 104 taken along line B-B of FIG. 1. In the illustrated example, the container 104 is in a third position in which the container is fully inserted into the cradle 102. Additionally, the sliding lock 414 is in the engaged or second position. Once the container 104 is fully inserted, the latch 118 extends inward toward a center of the cradle 102 and over the flange 314 of the cap 200, thereby preventing the container 104 from being release from the cradle 102 (e.g., via the force of the first and second springs 448, 450 (FIG. 4)). The latch 118 is movable along the third axis 453, which is perpendicular to the first axis 419 along which the sliding lock 414 moves. To bias the latch 118 inward toward a center the cradle 102, a spring 1000 is coupled between the latch 118 and the side wall 108. In the illustrated example, the drain probe 400 and the vent probe 408 extend through the opening 418 in the sliding lock 414, through the opening 302 of the cap 200 (and the septum 310), and into the opening 800 of the container 104. The contents of the container 104 can then be drained through the drain probe 400. Positive pressure air may be provided through the vent probe 408 to prevent a vacuum from forming inside of the container 104. In the illustrated example, the vent probe 408 is longer or extends further than the drain probe 400. However, in other examples, the probes 400, 408 may be equal lengths or heights. In other examples, the probes 400, 408 may be longer or shorter and, thus, extend into the container 104 further or extend into the container 104 less.

In the illustrated example, the sensor 128 measures the level of liquid in the container 104. The sensor 128 may detect when liquid contents of the container 104 are low and/or empty. In the illustrated example, the sensor 128 is a capacitive sensor, which can sense through the wall of the housing 105 and through the wall of the container 104 to sense a level of liquid within the container 104. In other examples, other types of liquid sensors may be implemented.

When the container 104 is empty, or it is desired to remove the container 104 (such as for example, upon a recall or an expiration of the contents of the container 104), the release button 120 may be depressed or pushed downward. As the release button 120 moves downward, the beveled edge 456 of the release button 120 engages the beveled edge 454 of the latch 118 and forces the latch 118 to retract, outward, along the third axis 453. In the illustrated example, a spring 1002 is disposed in the release button channel 122 that biases the release button 120 upwards or away from the latch 118. When the latch 118 is moved outward or away from the center of the cradle 102, the latch 118 clears the flange 314 and the sliding lock 414 is able to move upwards away from the bottom wall 106 to eject the container 104 (e.g., via the force of the first spring 458 (FIG. 4)).

In the illustrated example, and as illustrated in FIGS. 6A and 6B, the sliding lock 414 has a first tab 616 and a second tab 618 (e.g., ears) that project or extend outward from the outer wall 420. When assembling the cradle 102, the sliding lock 414 is inserted into the housing 105 and the first and second tabs 616, 618 flex inward. Once inserted, the first and second tabs 616, 618 project outward into respective first and second slots 1004, 1006 in the side wall 108. The first and second tabs 616, 616 prevent the sliding lock 414 from being forced (e.g., via the first spring 448) upward and out of the housing 105. In some examples, a tool is needed to bend the first and second tabs 616, 618 back inwards to remove the sliding lock 414 from the housing 105. As illustrated in FIG. 10, the cradle 102 has a drain barb 1008 extending from the bottom wall 106. The drain barb 1008 enables liquid to be drained from the bottom of the housing 105 if any excess liquid is spilled into the bottom of the housing 105, for example.

Figure 11:
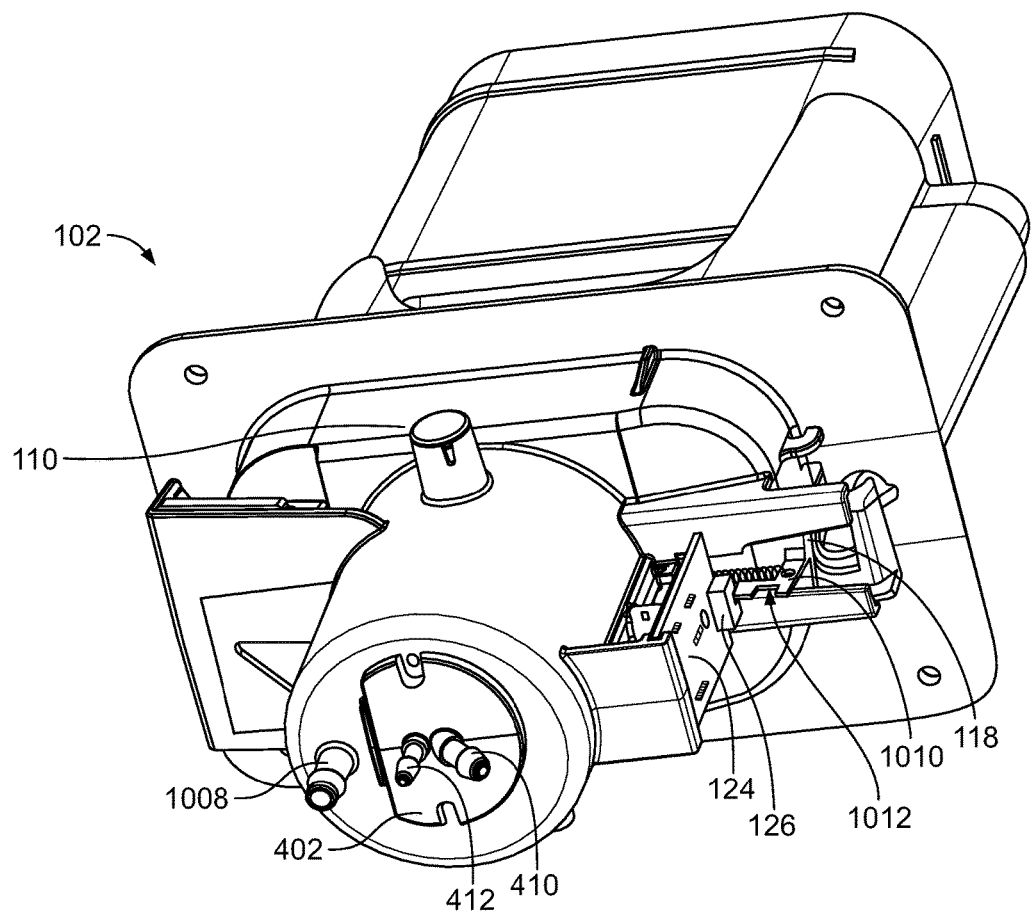
FIG. 11 is a bottom perspective view of the example cradle of FIG. 1 illustrating an example latch for securing the example container in the example cradle.
Figure 12:
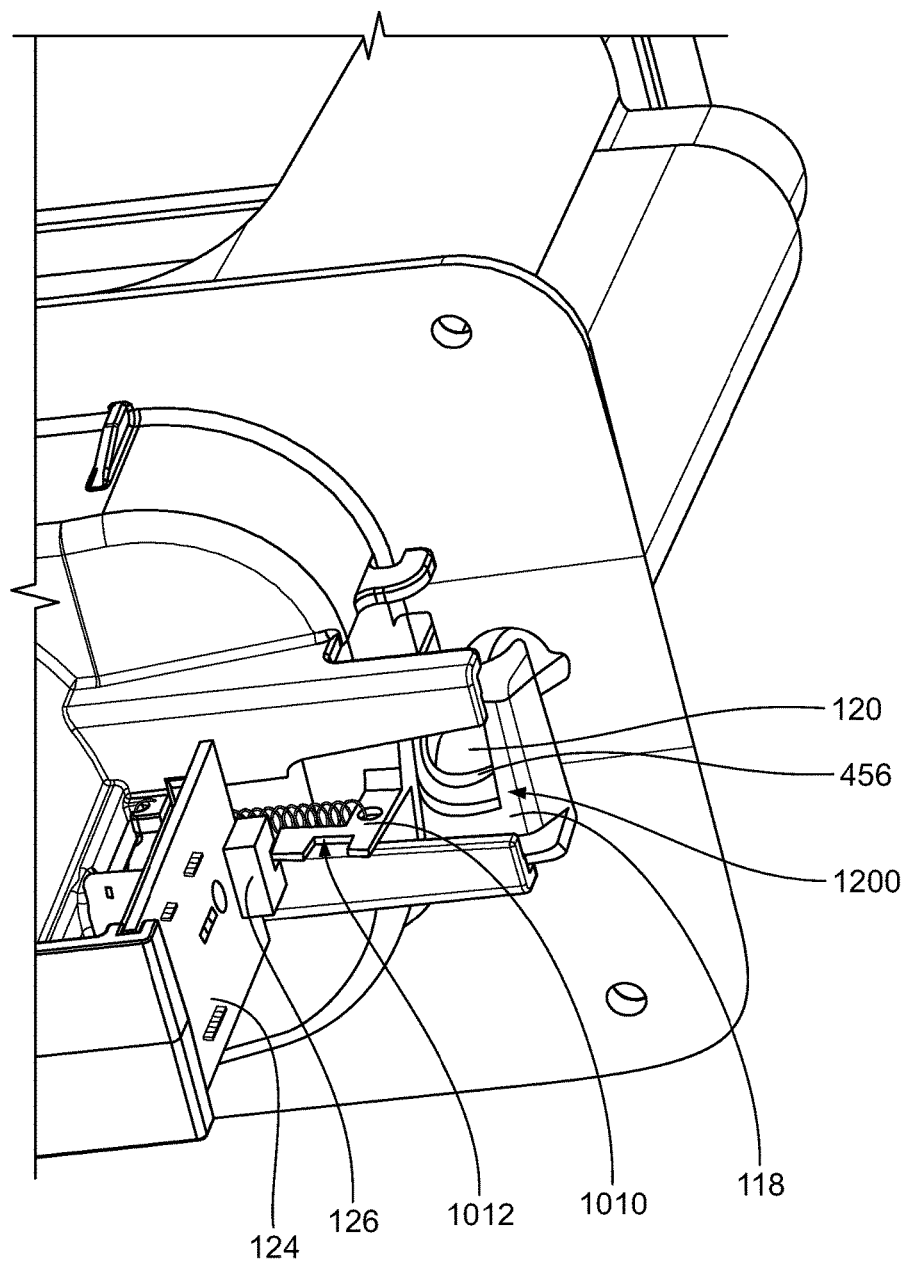
FIG. 12 is an enlarged view of the example latch of FIG. 11.

FIG. 11 shows a bottom perspective view of the cradle 102 and FIG. 12 shows an enlarged view of the latch 118 as illustrated in FIG. 11. The container holder 110, the first and second barbs 410, 412, the probe mount 402 and the drain barb 1008 are shown in FIG. 11. As illustrated in FIG. 12, the latch 118 has an opening 1200 to receive the beveled edge 456 of the release button 120 as the release button 120 is pushed downward.

As illustrated in FIGS. 10-12, the latch 118 has a leg 1010 with a notch 1012. The leg 1010 is received by the position sensor 126. The sensor 126 determines the position of the latch 118 (e.g., based the location of the notch 1012). When the latch 118 is fully engaged (as in the position illustrated in FIG. 10), the sensor 126 may determine that the latch 118 is properly engaged and the container 104 is secure within the cradle 102. Otherwise, the sensor 126 may determine that the latch 118 is partially engaged (e.g., when the sliding lock 414 is moved toward the bottom wall 106) and/or not engaged (e.g., when the release button 120 is depressed and the latch 118 is fully retracted, when the siding lock 414 is in the uppermost position and the latch 118 is engaging the outer wall 420 of the sliding lock 414). In some examples, the position sensor 126 is an optical sensor. In other examples, other types of sensors may be implemented. The position sensor 126 and the level sensor 128 are communicatively coupled (e.g., via wires or wirelessly) to the circuit board 124.

Figure 13:
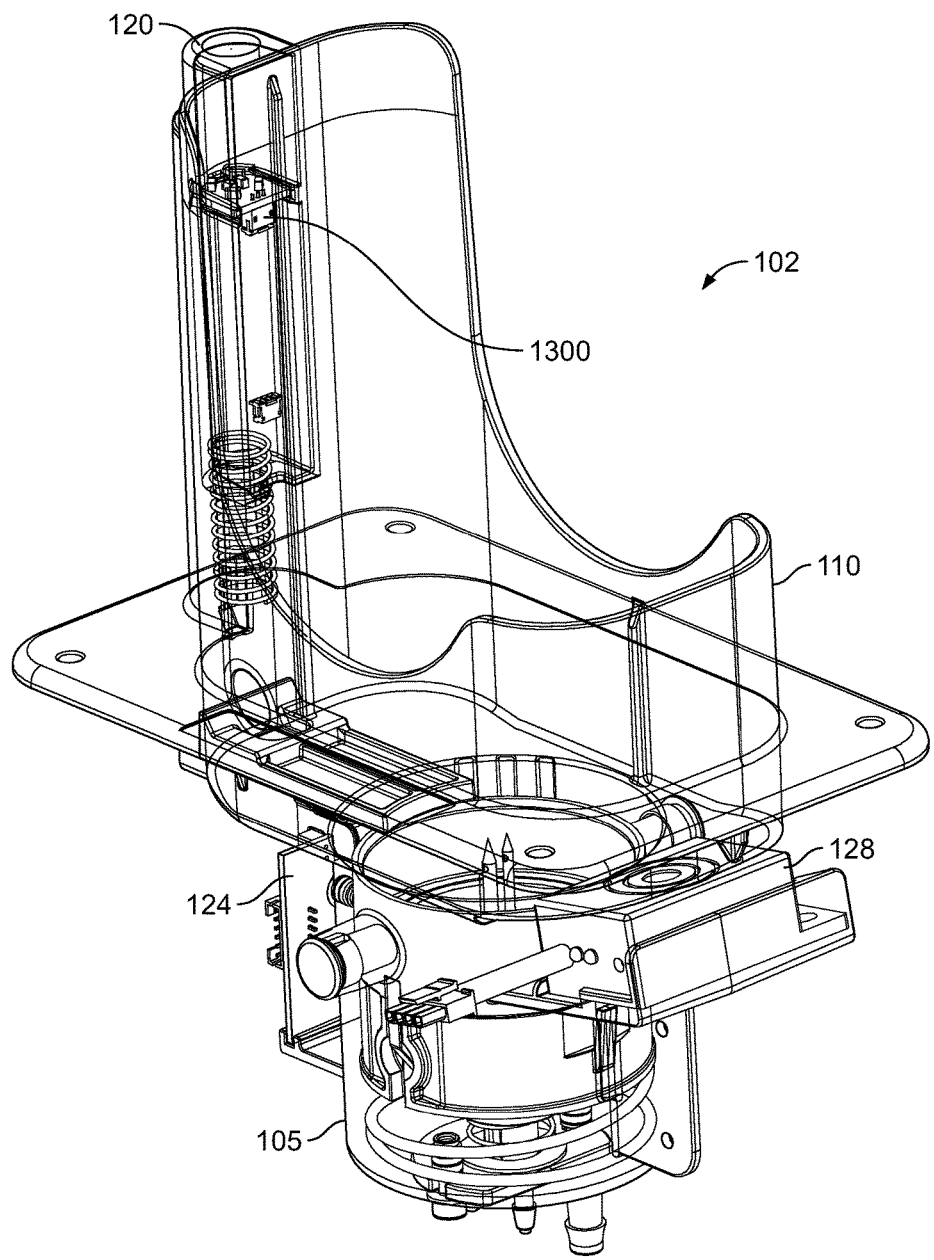
FIG. 13 is a perspective view of the example cradle of FIG. 1 illustrating an example light disposed within a release button.

In some examples, one or more lights are provided in the release button 120 to indicate different states or statuses of the container 104 and/or the cradle 102. FIG. 13 illustrates the example cradle 102 in which the housing 105 and the container holder 110 are shown as transparent. In the illustrated example, a light 1300 is disposed within the release button 120. The light 1300 may blink or illuminate and/or use different colors depending on the state of the container 104 and/or the cradle 102. For example, when the container 104 is fully inserted and the latch 118 is in the locked position (FIGS. 10-12), the release button 120 may be illuminated a certain color (e.g., green) by the light 1300. In some examples, when the container 104 is empty or the liquid level is low (e.g., as detected by the sensor 128), the release button 120 may be illuminated another color (e.g., red) by the light 1300. Additionally or alternatively, different sequences of a blinking light may be used to indicate the different states or status. In some examples, the release button 120 is transparent or semi-transparent. In some examples, then light 1300 is a light emitting diode (LED). In some examples, more than one light is implemented (e.g., multiple LEDs). Some examples may include a display to present human-readable indicia regarding such states or status. The light 1300 is communicatively coupled (e.g., via a wire or wirelessly) to the circuit board 124.

Figure 14A:
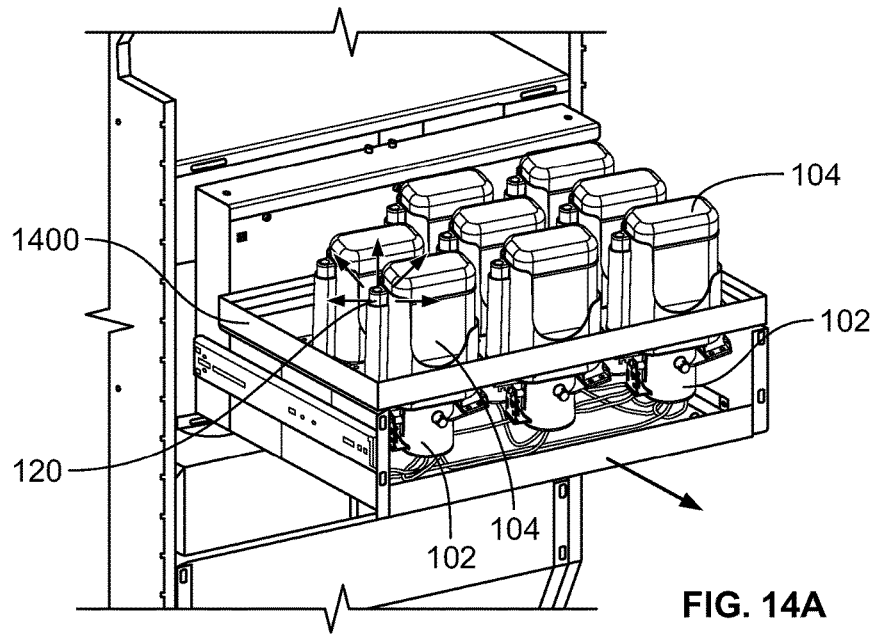
FIGS. 14A-14C illustrate an example sequence of removing an example container from an example cradle in an example drawer of an automated diagnostic analyzer having multiple ones of the example cradle of FIG. 1.
Figure 14B:
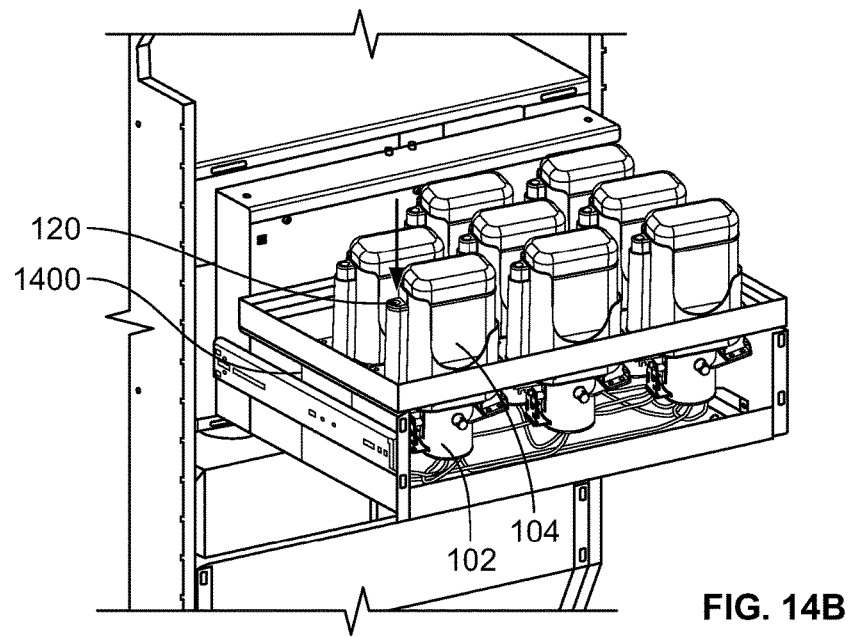
Figure 14C:
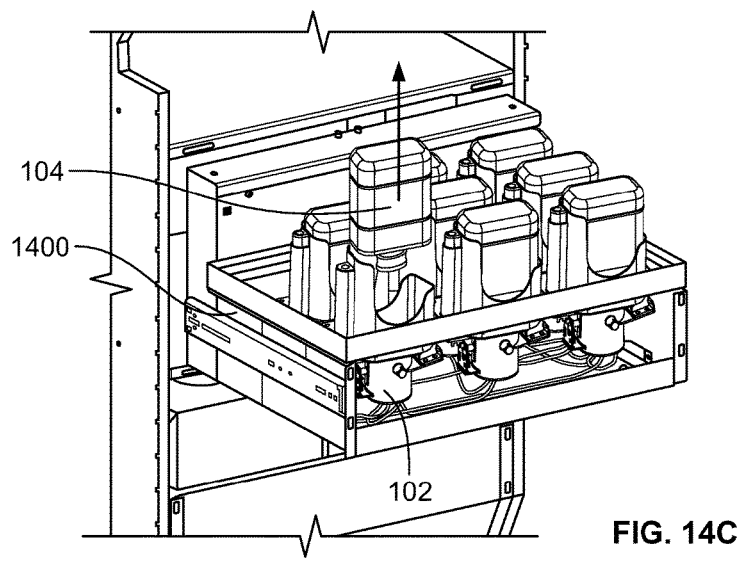

FIGS. 14A-14C illustrate an example drawer 1400 of an automated diagnostic analyzer or instrument having multiple ones of the cradle 102. The drawer 1400 may be part of a body or chassis of automated diagnostic analyzer or instrument and may be pulled out to check, add or replace containers to the cradles 102. Each of the cradles 102 may connect to the same or different onboard tanks that are to be filled with the liquid in the containers 104. In the illustrated example, the cradles 102 are arranged in a 3 by 3 pattern or grid with eight cradles 102 (e.g., there is one empty spot). In other examples, the drawer 1300 may have more or fewer cradles 102 and/or the cradles 102 may be arranged in different configurations (e.g., a 4 by 4 pattern). The cradles 102 may be configured to accept the same type of cap or different caps. For example, one or more of the cradles 102 may have a sliding lock (e.g., the sliding lock 414 of FIG. 4) that only accepts the caps 200 of FIG. 2B, which have medium diameter key rings 202, while other ones of the cradles 102 may have a sliding lock that only accepts the caps 200 of FIG. 2C, which has the largest diameter key ring 202. Thus, the wrong liquid containers cannot be fully inserted into the wrong cradles 102.

In some examples, when the container 104 is empty, the release button 120 of the corresponding cradle 102 may illuminate (e.g., via the example light 1300 as illustrated in FIG. 13). In some examples, the release button 120 illuminates different colors to indicate different states of the operation. For example, the release button 120 may illuminate a particular color (e.g., red) when the corresponding container 104 is empty or low. In some examples, the release button 120 may illuminate another color (e.g., yellow) when the container 104 is not fully inserted or incorrectly inserted (e.g., in the position illustrated in FIG. 9).

As illustrated in FIG. 14B, the release button 120 may be depressed to release the latch (e.g., the latch 118 of FIG. 4) of the corresponding cradle 102 to eject the container 104. As illustrated in FIG. 14C, once released, the container 104 can then be removed from the corresponding cradle 102. Another container (e.g., having the appropriate the matching cap) can be inserted into the cradle 102 and pushed into the cradle 102 to couple the replacement container to the cradle 102.

Figure 15:
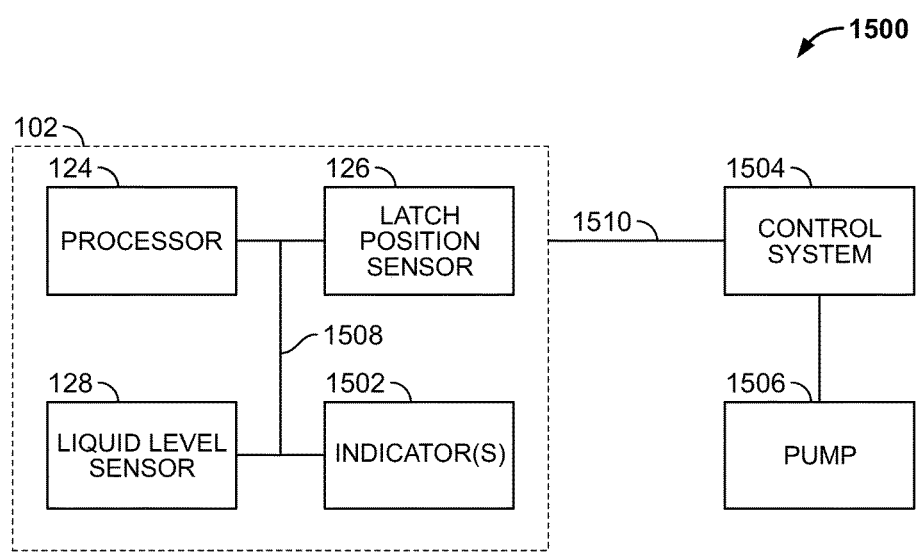
FIG. 15 is a block diagram of an example bulk solution system employing the example cradle of FIG. 1.

FIG. 15 is a block diagram of an example bulk solution system 1500 that may be used to supply a liquid (e.g., a bulk solution liquid for an automated diagnostic analyzer) from a first bottle or container to another bottle or container (e.g., an onboard tank). In the illustrated example, the bulk solution system 1500 includes the cradle 102 having the circuit board or processor 124, the latch position sensor 126, the liquid level sensor 128, and one or more indicator(s) 1502 such as, for example, a light.

In the illustrated example, the latch position sensor 126 senses or measures the position of the latch 118 (FIG. 1). The latch position sensor 126 may sense if the latch 118 is in one or more positions. For example, the latch position sensor 126 may sense if the latch 118 is in a fully engaged position (as illustrated in FIG. 10), a partially engaged (e.g., when the sliding lock 414 (FIG. 9) is moved toward the bottom wall 106) and/or not engaged (e.g., when the sliding lock 414 is in the upper position as illustrated in FIG. 8). The latch position sensor 126 is communicatively coupled to the processor 124. The processor 124 may be used to control the indicator(s) 1502 to indicate the position of the latch 118 as sensed by the latch position sensor 126. The indicator(s) 1502 may correspond to, for example, the light(s) 1300 (FIG. 13) that illuminate (e.g., blink or illuminate continuously) different colors depending on the position of the latch 118.

In the illustrated example, the liquid level sensor 128 senses or measures the level of liquid of remaining in the container 104 (FIG. 1). The liquid level sensor 128 is communicatively coupled to the processor 124. The processor 124 may be used to control the indicator(s) 1502 to indicate when the level of liquid is low as sensed by the liquid level sensor 128. For example, when the liquid level sensor 128 determines the remaining liquid is below a threshold, the processor 124 may control the indicator(s) 1300 to illuminate (e.g., blink red or yellow).

In the illustrated example, the cradle 102 is communicatively coupled to a control system 1504. The control system 1504 may be a system used to control an automated diagnostic analyzer, for example. The control system 1504 is communicatively coupled to a pump 1506. When a container is fully and properly inserted into the cradle 102, the processor 124 transmits a message to the control system 1504 that the container is ready to be drained. The control system 1504 controls the pump 1506 to pump the contents of the container 104 (via the drain probe 400) from the container 104 to an onboard tank. In other examples, the cradle 102 may be communicatively coupled directly to the pump and may control the pump directly.

In the illustrated example, the latch position sensor 126, the liquid level sensor 128 and the indicator(s) 1502 are communicatively coupled to the processor 124 (and/or to each other) via communication links 1508, and the cradle is communicatively coupled the control system 1504 and the pump 1506 via communication links 1510. The communication links 1508, 1510 may be any type of wired connection (e.g., a databus, a USB connection, etc.) or a wireless communication mechanism (e.g., radio frequency, infrared, etc.) using any past, present or future communication protocol (e.g., Bluetooth, USB 2.0, USB 3.0, etc.).

While an example manner of implementing the bulk solution system 1500 is illustrated in FIG. 15, one or more of the elements, processes and/or devices illustrated in FIG. 15 may be combined, divided, re-arranged, omitted, eliminated and/or implemented in any other way. Further, the example processor 124, the example latch position sensor 126, the example liquid level sensor 128, the example indicator(s) 1502, the example control system 1504, the example pump 1506 and/or, more generally, the example bulk solution system 1500 of FIG. 15 may be implemented by hardware, software, firmware and/or any combination of hardware, software and/or firmware. Thus, for example, any of the example processor 124, the example latch position sensor 126, the example liquid level sensor 128, the example indicator(s) 1502, the example control system 1504, the example pump 1506 and/or, more generally, the example bulk solution system 1500 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example processor 124 and/or the example control system 1504 is/are hereby expressly defined to include a tangible computer readable storage device or storage disk such as a memory, a digital versatile disk (DVD), a compact disk (CD), a Blu-ray disk, etc. storing the software and/or firmware. Further still, the example bulk solution system 1500 of FIG. 15 may include one or more elements, processes and/or devices in addition to, or instead of, those illustrated in FIG. 15, and/or may include more than one of any or all of the illustrated elements, processes and devices.

Figure 16:
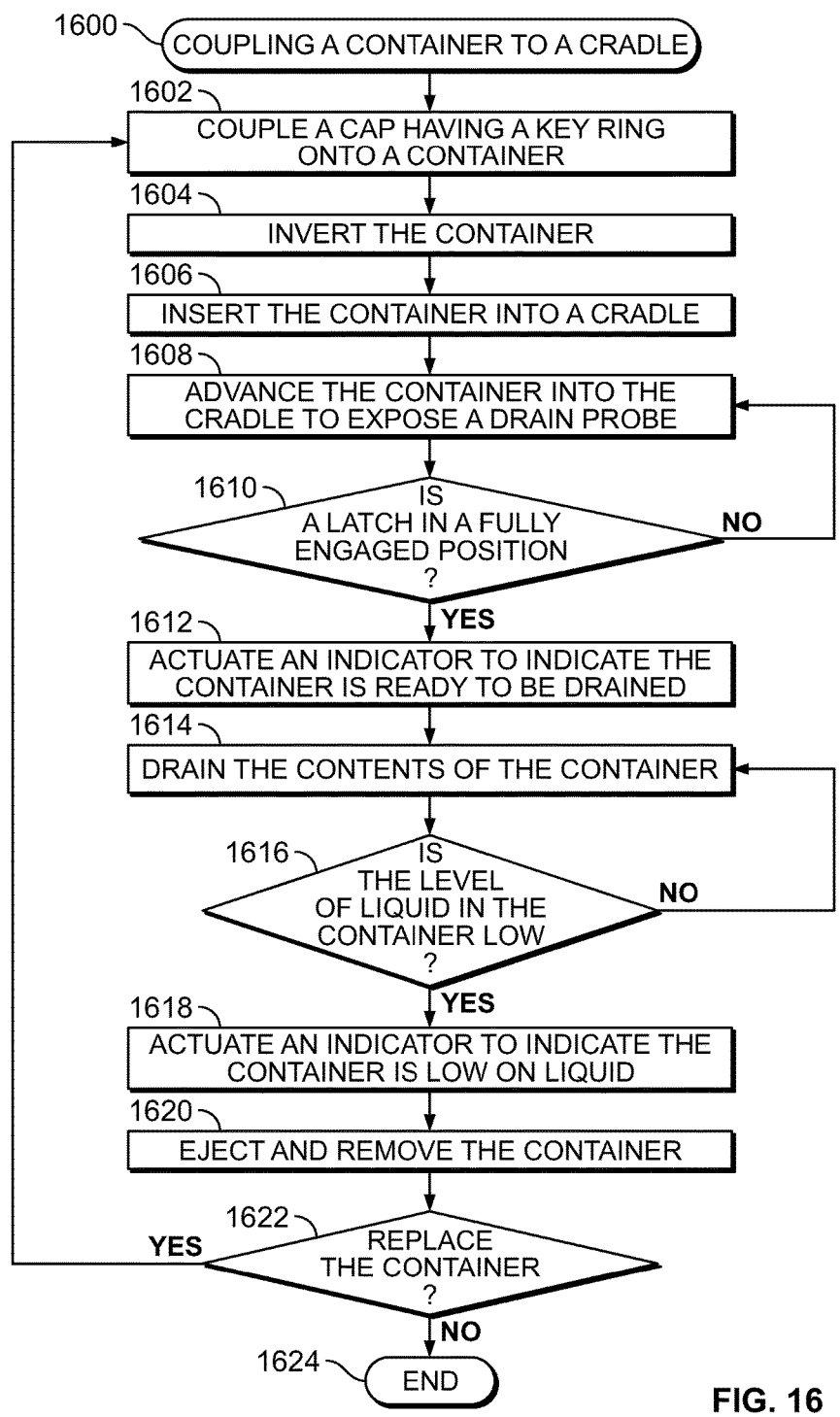
FIG. 16 is a flowchart illustrating an example method of inserting a container into a cradle to drain the container, which may be implemented using the example cradle of FIG. 1 and/or the example bulk solution system of FIG. 15.

A flowchart representative of example method for implementing the example bulk solution system 1500 is shown in FIG. 16. In this example, the method may be implemented using machine readable instructions that comprise a program for execution by a processor such as the processor 1712 shown in the example processor platform 1700 discussed below in connection with FIG. 17. The program may be embodied in software stored on a tangible computer readable storage medium such as a CD-ROM, a floppy disk, a hard drive, a digital versatile disk (DVD), a Blu-ray disk, or a memory associated with the processor 1712, but the entire program and/or parts thereof could alternatively be executed by a device other than the processor 1712 and/or embodied in firmware or dedicated hardware. Further, although the example program is described with reference to the flowchart illustrated in FIG. 16, many other methods of implementing the example bulk solution system 1500 may alternatively be used. For example, the order of execution of the blocks may be changed, and/or some of the blocks described may be changed, eliminated, or combined.

As mentioned above, the example method of FIG. 16 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example method of FIG. 16 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 16 is a flowchart representative of an example method 1600 of coupling a container to a cradle, which may be used for transferring liquid from the container to another container, and which may be implemented (at least in part) using the example cradle 102 of FIG. 1 and/or the bulk solution system 1500 of FIG. 15. In the illustrated example, the method 1600 includes coupling a cap having a key ring onto a container (1602). For example, one of the caps 200 (FIG. 2) may be threadably coupled to the container 104 (FIG. 1). In other examples, the cap 200 may be coupled to the container 104 via other coupling techniques. In some examples, no cap is used. Instead, the container 104 may include a key ring extending from the container 104 (e.g., at or near the mouth 800).

The example method 1600 includes inverting the container (1604) and inserting the container into a cradle (block 1606). For example, as illustrated in FIGS. 8, 9 and 10, the container 104 is inverted (e.g., turned upside down) and inserted into the cradle 104. If the cap 200 has the correct key ring 202, the key ring 202 extends through the key slot 446 to engage the trigger 438. In some examples, the container 104 may be inserted into or otherwise fluidly coupled to the cradle 102 without inversion.

The example method 1600 includes advancing the container into the cradle to expose a drain probe (block 1608). For example, as illustrated in FIGS. 8, 9 and 10, as the container 104 is advanced into the cradle 102, the key ring 202 pushes the trigger 438 to disengage the first and second lockouts 422, 424, thereby enabling the sliding lock 414 to move toward the bottom wall 106. As the container 104 and the sliding lock 414 move downward, the drain probe 400 extends through the opening 418 of the sliding lock 414 to pierce the cap 200.

The example method 1600 includes determining whether a latch is in a fully engaged position (block 1610). If the latch is not in a fully engaged position, the container is to be advanced further into the cradle (block 1608). If the latch is in the fully engaged position, then an indicator is activated such as, for example, illuminating a light to indicate that the container is ready to be drained (block 1612). For example, as illustrated in FIG. 10, the latch 118 is in a fully engaged position where the latch 118 extends over the flange 314 on the cap 200 to secure the container 104 within the cradle 102. The latch position sensor 126 determines the position of the latch 118. If the latch 118 is fully engaged, the indicator(s) 1502 (FIG. 15) may be actuated (e.g., via a command from the processor 124) to indicate the container 104 is properly inserted into the cradle 102 and ready to be drained. In some examples, if the latch 118 is not fully engaged, then another indicator 1502 (e.g., another color light) may be actuated to indicate the container 104 has not been fully inserted into the cradle 102. In the illustrated example of FIGS. 1-14B the indicator 1502 may correspond to the light(s) 1300 (FIG. 13), which is disposed within the release button 120. However, in other examples, the indicator 1502 may be disposed in a different location on or near the cradle 102.

In the illustrated example of FIG. 16, the method 1600 includes draining the contents of the container (block 1614). In some examples, the contents of the container 104 may be drained via gravity. In other examples, such as illustrated in FIG. 15, the pump 1506 may be used to pump the liquid contents from the container 104. The pump 1506 may be controlled by the control system 1504 and/or the processor 126 of the cradle 102.

The example method 1600 includes determining if the level of liquid in the container is low (block 1616). If the level of liquid is not low, then the contents of the container may be drained (block 1614) as desired. If the level of liquid is low or empty, then an indicator is actuated to indicate the container is low on liquid (block 1618). For example the cradle 102 includes the liquid level sensor 128 to sense a level of liquid remaining in the container 104. If the level of liquid is low, then the indicator 1502 (FIG. 15) may be actuated (e.g., a different color light is illuminated than the color used to indicate the latch 118 is fully engaged). For example, the indicator 1502 may be a light (e.g., the light 1300 (FIG. 13) that blinks red or yellow.

The example method 1600 includes ejecting and removing the container from the cradle (block 1620) by, for example, pushing a release button. For example, as illustrated in FIGS. 14A-14C, the release button 120 is pushed to eject the container 104 from the cradle 102. Another container having a cap with the correct key ring may then be inserted into the cradle 102. In some examples, the motion of inserting the container 104 into the cradle 102 and pushing the container 104 down until the latch 118 is in the fully engaged position is performed on continuous motion (e.g., by an operator or technician).

The example method 1600 includes determining if the container is to be replaced (block 1622) with, for example, an additional container having the same or different contents. If the container is to be replaced, the example method 1600 continues with coupling a cap having a key to the new or replacement container (block 1602), and so forth. If the container is not to be replaced (block 1622), the example method 1600 ends (block 1624).

Figure 17:
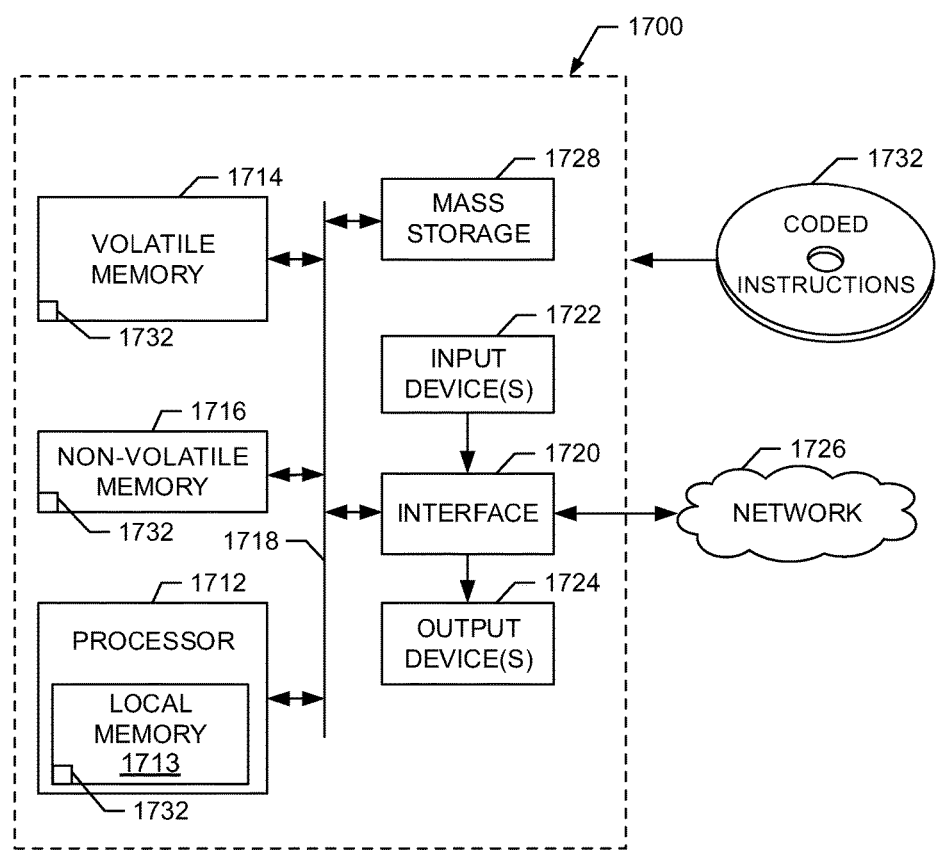
FIG. 17 is a diagram of a processor platform for use with the examples disclosed herein.

FIG. 17 is a block diagram of an example processor platform 1700 capable of executing instructions to implement the method 1600 of FIG. 16 and example bulk solution system 1500 of FIG. 15. The processor platform 1700 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, or any other type of computing device.

The processor platform 1700 of the illustrated example includes a processor 1712. The processor 1712 of the illustrated example is hardware. For example, the processor 1712 can be implemented by one or more integrated circuits, logic circuits, microprocessors or controllers from any desired family or manufacturer.

The processor 1712 of the illustrated example includes a local memory 1713 (e.g., a cache). The processor 1712 of the illustrated example is in communication with a main memory including a volatile memory 1714 and a non-volatile memory 1716 via a bus 1718. The volatile memory 1714 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1716 may be implemented by flash memory and/or any other desired type of memory device. Access to the main memory 1714, 1716 is controlled by a memory controller.

The processor platform 1700 of the illustrated example also includes an interface circuit 1720. The interface circuit 1720 may be implemented by any type of interface standard, such as an Ethernet interface, a universal serial bus (USB), and/or a PCI express interface.

In the illustrated example, one or more input devices 1722 are connected to the interface circuit 1720. The input device(s) 1722 permit(s) a user to enter data and commands into the processor 1712. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1724 are also connected to the interface circuit 1720 of the illustrated example. The output devices 1724 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1720 of the illustrated example, thus, typically includes a graphics driver card, a graphics driver chip or a graphics driver processor.

The interface circuit 1720 of the illustrated example also includes a communication device such as a transmitter, a receiver, a transceiver, a modem and/or network interface card to facilitate exchange of data with external machines (e.g., computing devices of any kind) via a network 1726 (e.g., an Ethernet connection, a digital subscriber line (DSL), a telephone line, coaxial cable, a cellular telephone system, etc.).

The processor platform 1700 of the illustrated example also includes one or more mass storage devices 1728 for storing software and/or data. Examples of such mass storage devices 1728 include floppy disk drives, hard drive disks, compact disk drives, Blu-ray disk drives, RAID systems, and digital versatile disk (DVD) drives.

Coded instructions 1732 to implement the method 1600 of FIG. 16 may be stored in the mass storage device 1728, in the volatile memory 1714, in the non-volatile memory 1716, and/or on a removable tangible computer readable storage medium such as a CD or DVD.

While the example cradles disclosed herein were described in connection with bulk solution liquids for an automated diagnostic analyzer, the example cradles may be used in any application where a liquid is to be drain from a bottle, inverted or upright. From the foregoing, it will be appreciated that the above disclosed cradles provide a relatively safer means for piercing a cap and/or septum on a container and draining the liquid contents therein. The example cradles employ a unique locking system that prevents bottles having the wrong caps from being inserted into the cradles and drained (e.g., by mistake). Further, the example cradles include sensors that determine whether a container is fully and property inserted into a cradle and/or the level of liquid remaining within the container.

Although certain example apparatus and methods, and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
a housing having a bottom and an open top, the housing to receive a container having liquid;
a probe extending upward from the bottom toward the open top, the probe to drain the liquid from the container when the probe is inserted into the container;
a sliding lock slidably disposed within the housing, the sliding lock including:
an engagement surface;
an opening in the engagement surface to receive the probe therethrough when the sliding lock is moved from a first position in which the engagement surface is above a tip of the probe to a second position in which the engagement surface is below the tip of the probe; and
a key slot in the engagement surface; and
means for preventing movement of the sliding lock in the housing until a container key is inserted into the key slot of the sliding lock.

2. The apparatus of claim 1, wherein the means for preventing movement is disposed between the engagement surface and the bottom of the housing.

3. The apparatus of claim 1, further including means for releasably securing the container to the housing once the container is inserted into the housing.

4. The apparatus of claim 3, further including means for biasing the container upward to eject the container from the housing after the means for releasably securing is released.

5. The apparatus of claim 1, further including means for indicating when the container is fully inserted into the housing.

6. The apparatus of claim 1, further including means for determining a level of the liquid within the container.

7. The apparatus of claim 6, further including means for indicating when the level of the liquid is low or the container is empty.

8. An apparatus comprising:
a housing having a bottom wall, a side wall and an open top, the housing to receive a container having liquid;
a probe extending from the bottom wall toward the open top; and
a sliding lock slidably disposed within the housing, the sliding lock operable between a locked state in which movement of the sliding lock is prevented and an unlocked state in which the sliding lock is movable toward the bottom wall of the housing to enable the probe to be inserted into a cap of the container, the sliding lock further including a key slot, the sliding lock operable in the unlocked state when a key on the cap having a shape that corresponds to the key slot is inserted into the key slot.

9. The apparatus of claim 8, wherein the sliding lock includes an opening to receive the probe therethrough when the sliding lock is moved toward the bottom wall of the housing.

10. The apparatus of claim 8, further including a lockout that is movable between a locked position in which the lockout prevents the sliding lock from moving in the locked state and an unlocked position in which the sliding lock enables the sliding lock to move in the unlocked state.

11. The apparatus of claim 10, wherein the lockout is disposed between an engagement surface of the sliding lock and the bottom wall of the housing.

12. The apparatus of claim 10, further including a trigger disposed in the housing below the sliding lock, the trigger engageable with the key to move the trigger toward the bottom wall of the housing to move the lockout to the unlocked position.

13. The apparatus of claim 10, wherein the lockout is moveable in an opening formed in the side wall of the housing.

14. The apparatus of claim 13, wherein the lockout is a first lockout, further including a second lockout coupled to the side wall of the housing opposite the first lockout.

15. The apparatus of claim 8, further including a latch to engage a rim on the container or the cap of the container to releasably secure the container in the housing when the container is inserted into the housing.

16. The apparatus of claim 15, further including a release button to release the latch from the container or the cap of the container when the release button is activated.

17. The apparatus of claim 16, further including a light disposed in the release button, the light to illuminate the release button when the container is fully inserted into the housing and the latch is in a locked position.

18. The apparatus of claim 16, wherein the sliding lock is movable along a first axis and the release button is movable along a second axis parallel to the first axis.

19. The apparatus of claim 18, wherein the housing is a first housing, and wherein the release button is disposed within a second housing along a side of the first housing.

20. The apparatus of claim 8, wherein the key slot is a ring-shaped slot.

* * * * *